United States Patent
Yoshida et al.

(10) Patent No.: US 8,309,512 B2
(45) Date of Patent: Nov. 13, 2012

(54) PLATELET AGGREGATION INHIBITOR COMPOSITION

(75) Inventors: Shigeto Yoshida, Shimotsuke (JP); Toshiki Sudo, Sokushima (JP)

(73) Assignees: Educational Foundation Jichi Medical University, Tochigi (JP); Otsuka Pharmaceutical Co., Ltd, Tokyo (JP)

( * ) Notice: Subject to any disclaimer, the term of this patent is extended or adjusted under 35 U.S.C. 154(b) by 0 days.

(21) Appl. No.: 13/215,004

(22) Filed: Aug. 22, 2011

(65) Prior Publication Data

US 2012/0004186 A1     Jan. 5, 2012

Related U.S. Application Data

(62) Division of application No. 12/065,701, filed as application No. PCT/JP2006/322417 on Nov. 2, 2006, now Pat. No. 8,034,763.

(30) Foreign Application Priority Data

Nov. 4, 2005   (JP) ................................. 2005-320817

(51) Int. Cl.
*A61K 38/00* (2006.01)
*A61P 7/00* (2006.01)
*A61K 38/36* (2006.01)
*A61P 7/02* (2006.01)
*C07K 7/02* (2006.01)
*C07K 14/00* (2006.01)
*C07H 21/04* (2006.01)

(52) U.S. Cl. .......... 514/1; 514/13.5; 514/13.7; 530/350; 536/23.5

(58) Field of Classification Search ........................ None
See application file for complete search history.

(56) References Cited

FOREIGN PATENT DOCUMENTS

| JP | 2003-116573 A | 4/2003 |
|---|---|---|
| JP | 2004-121086 A | 4/2004 |
| JP | 2004-121091 A | 4/2004 |
| WO | 9608563 A1 | 3/1996 |

OTHER PUBLICATIONS

Bruno Arca et al., "An updated catalogue of salivary gland transcripts in the adult female mosquito, *Anopheles gambiae*", The Journal of Experimental Biology, 2005, 208: 3971-3986.
Database EMBL [online], "Anopheles stephensi ansg-1 mRNA for GE rich salivary gland protein, complete cds", Jul. 3, 2003.
J. M. C. Ribeiro, "Role of Mosquito Saliva in Blood Vessel Location", Journal of Experimental Biology, 1984, 108: 1-7.
UniProtKB/TrEMBL Q7YT37, Anti-platelet aggregation protein—*Anopheles stephensi* (Indo-Pakistan malaria mosquito), retrieved only from //www.uniprot.org/uniprot/Q7YT37.html, Mar. 1, 2004.
Jesus G. Valenzuela et al., "Purification, Cloning, and Síntesis of a Novel Salivary Anti-thrombin from the Mosquito *Anopheles albimanus*", Biochemistry, 1999, 38: 11209-11215.

(Continued)

*Primary Examiner* — Cherie M Stanfield
(74) *Attorney, Agent, or Firm* — Sughrue Mion, PLLC

(57) ABSTRACT

The invention provides a pharmaceutical composition comprising at least one polypeptide of the following (a) to (d):
(a) a polypeptide comprising the amino acid sequence of SEQ ID NO:1;
(b) a polypeptide comprising an amino acid sequence comprising one or more amino acid deletions, insertions, substitutions or additions in the amino acid sequence of the above (a) and having a platelet aggregation inhibitory activity and/or a platelet adhesion inhibitory activity;
(c) a polypeptide comprising the amino acid sequence of SEQ ID NO:3; and
(d) a polypeptide comprising an amino acid sequence comprising one or more amino acid deletions, insertions, substitutions or additions in the amino acid sequence of the above (c) and having a platelet aggregation inhibitory activity and/or a platelet adhesion inhibitory activity,
as an active component.

8 Claims, 2 Drawing Sheets

Time course

OTHER PUBLICATIONS

Jesus G. Valenzuela et al., "Exploring the salivary gland transcriptote and proteome of the *Anopheles stephensi* mosquito", Insect Biochemistry and Molecular Biology, 2003, 33: 717-732.

H. Watanabe et al., "Cloning of a gene encoding for GE-rich protein of salivary gland of *Anopheles Stephens*", Medical Entomology and Zoology, 2004, 55(Suppl.): 41.

S. Yoshida et al, "Robust salivary gland-specific transgene expression in *Anopheles stephensi* mosquito", Insect Molecular Biology, 2006, 15(4): 403-410.

Shigeto Yoshida et al, "Inhibition of collagen-induced platelet aggregation by anopheline antiplatelet protein, a saliva protein from a malaria vector mosquito", Blood, 2008, 111(4): 2007-2014.

SEQUENCE LISTING

```
<160> NUMBER OF SEQ ID NOS: 16

<210> SEQ ID NO 1
<211> LENGTH: 248
<212> TYPE: PRT
<213> ORGANISM: Anopheles stephensi
```

<400> SEQUENCE: 1

```
Ser Asp Glu Thr Thr Asp Gln Glu Ser Ser Thr Glu Leu Ser Glu Asp
1               5                   10                  15
Thr Ser Asp Ser Tyr His Gln Glu Glu Asp Thr Ser Glu Thr Gly Ala
            20                  25                  30
Asp Ala Gly Thr Glu Asp Gly Asn Ser Glu Asp Ser Ser Glu Leu
        35                  40                  45
Glu Ser Ser Glu Glu Gly His Glu Asp Gly Ser Glu Asp Ala Thr
50                  55                  60
Gly Glu Glu Gly Gly Ala Gly Glu Lys Gly Glu Ala Gly Glu Glu Asp
65                  70                  75                  80
Glu Ala Gly Glu Glu Gly Glu Ala Gly Glu Glu Gly Glu Ala Gly Glu
                85                  90                  95
Glu Gly Gly Ala Gly Glu Glu Gly Gly Ala Gly Glu Glu Gly Gly Ala
            100                 105                 110
Asp Glu Glu Gly Ser Ala Gly Glu Glu Gly Gly Ala Gly Gly Gly Glu
            115                 120                 125
Glu Ser Pro Val Asn Thr Tyr His Gln Val His Asn Leu Leu Lys Asn
130                 135                 140
Ile Met Asn Val Gly Thr Lys Asn Asn Tyr Leu Lys Ser Phe Ile Leu
145                 150                 155                 160
Ala Arg Leu Gln Glu Arg Leu Met Asn Pro Thr Ile Asp Leu Val Gly
                165                 170                 175
Ser Ile Ser Lys Tyr Ser Lys Ile Lys Glu Cys Phe Asp Ser Leu Ala
            180                 185                 190
Asp Asp Val Lys Ser Leu Val Glu Lys Ser Glu Thr Ser Tyr Glu Glu
        195                 200                 205
Cys Ser Lys Asp Lys Asn Asn Pro His Cys Gly Ser Glu Gly Thr Arg
    210                 215                 220
Glu Leu Asp Glu Gly Leu Ile Glu Arg Glu Gln Lys Leu Ser Asp Cys
225                 230                 235                 240
Ile Val Glu Lys Arg Asp Ser Glu
                245
```

<210> SEQ ID NO 2
<211> LENGTH: 744
<212> TYPE: DNA
<213> ORGANISM: Anopheles stephensi

<400> SEQUENCE: 2

```
tccgacgaga ctacggatca agaatcatcg accgagctaa gcgaagacac ttcggatagc      60
taccaccagg aagaggatac atcagaaacc ggtgccgatg ctggtacaga ggacggtaat     120
tcggaagatg actccagcga attagaatct tcttcggaag aaggtcatga ggatggtagc     180
gaagacgcta ctggtgagga aggtggggca ggcgagaaag gtgaggccgg tgaggaagac     240
gaggcaggcg aggaaggtga ggcaggtgag gaaggtgaag caggtgaaga aggtggtgca     300
ggtgaagaag gcggagcagg tgaagaaggc ggtgcagacg aagaaggtag tgcaggtgaa     360
gaaggcggtg cagaaggtgg tgaagagtcc cccgttaata cctaccatca ggtgcacaac     420
ttgctgaaga acatcatgaa cgttggcacg aagaacaatt acttgaagtc gttcattttg     480
gcccgcctgc aggaacgtct catgaacccc acgatcgacc tggtcggcag tatctccaaa     540
tattccaaga ttaaggaatg cttcgactcg ctggccgacg atgtgaaatc tctggtggag     600
aagtccgaaa catcgtacga agagtgcagc aaggacaaga ataaccctca ctgcggcagt     660
```

-continued

```
gaaggtacac gcgagcttga cgagggactc atcgaacggg aacagaagct atcggattgc    720
atcgtcgaaa agcgtgattc agag                                           744
```

<210> SEQ ID NO 3
<211> LENGTH: 122
<212> TYPE: PRT
<213> ORGANISM: Anopheles stephensi

<400> SEQUENCE: 3

Gly Glu Glu Ser Pro Val Asn Thr Tyr His Gln Val His Asn Leu Leu
1               5                   10                  15

Lys Asn Ile Met Asn Val Gly Thr Lys Asn Asn Tyr Leu Lys Ser Phe
            20                  25                  30

Ile Leu Ala Arg Leu Gln Glu Arg Leu Met Asn Pro Thr Ile Asp Leu
        35                  40                  45

Val Gly Ser Ile Ser Lys Tyr Ser Lys Ile Lys Glu Cys Phe Asp Ser
    50                  55                  60

Leu Ala Asp Asp Val Lys Ser Leu Val Glu Lys Ser Glu Thr Ser Tyr
65                  70                  75                  80

Glu Glu Cys Ser Lys Asp Lys Asn Asn Pro His Cys Gly Ser Glu Gly
                85                  90                  95

Thr Arg Glu Leu Asp Glu Gly Leu Ile Glu Arg Glu Gln Lys Leu Ser
            100                 105                 110

Asp Cys Ile Val Glu Lys Arg Asp Ser Glu
        115                 120

<210> SEQ ID NO 4
<211> LENGTH: 366
<212> TYPE: DNA
<213> ORGANISM: Anopheles stephensi

<400> SEQUENCE: 4

```
ggtgaagagt cccccgttaa tacctaccat caggtgcaca acttgctgaa gaacatcatg    60
aacgttggca cgaagaacaa ttacttgaag tcgttcattt tggcccgcct gcaggaacgt   120
ctcatgaacc ccacgatcga cctggtcggc agtatctcca aatattccaa gattaaggaa   180
tgcttcgact cgctggccga cgatgtgaaa tctctggtgg agaagtccga acatcgtac    240 gaagagtgca gcaaggacaa gaataaccct cactgcggca gtgaaggtac acgcgagctt   300
gacgagggac tcatcgaacg ggaacagaag ctatcggatt gcatcgtcga aagcgtgat    360 tcagag                                                              366
```

<210> SEQ ID NO 5
<211> LENGTH: 269
<212> TYPE: PRT
<213> ORGANISM: Anopheles stephensi

<400> SEQUENCE: 5

Met Lys Leu Leu Leu Leu Leu Ala Ser Val Leu Cys Leu Ala Leu Ile
1               5                   10                  15

Val Ser Ala Arg Pro Ser Asp Glu Thr Thr Asp Gln Glu Ser Ser Thr
            20                  25                  30

Glu Leu Ser Glu Asp Thr Ser Asp Ser Tyr His Gln Glu Glu Asp Thr
        35                  40                  45

Ser Glu Thr Gly Ala Asp Ala Gly Thr Glu Asp Gly Asn Ser Glu Asp
    50                  55                  60

Asp Ser Ser Glu Leu Glu Ser Ser Glu Glu Gly His Glu Asp Gly
65                  70                  75                  80

Ser Glu Asp Ala Thr Gly Glu Glu Gly Ala Gly Glu Lys Gly Glu
                85                  90                  95

Ala Gly Glu Glu Asp Glu Ala Gly Glu Gly Glu Ala Gly Glu
            100                 105                 110

Gly Glu Ala Gly Glu Gly Gly Ala Gly Glu Gly Gly Ala Gly
            115                 120                 125

Glu Glu Gly Gly Ala Asp Glu Glu Gly Ser Ala Gly Glu Gly Gly
130                 135                 140

Ala Glu Gly Gly Glu Glu Ser Pro Val Asn Thr Tyr His Gln Val His
145                 150                 155                 160

Asn Leu Leu Lys Asn Ile Met Asn Val Gly Thr Lys Asn Asn Tyr Leu
                165                 170                 175

Lys Ser Phe Ile Leu Ala Arg Leu Gln Glu Arg Leu Met Asn Pro Thr
            180                 185                 190

Ile Asp Leu Val Gly Ser Ile Ser Lys Tyr Ser Lys Ile Lys Glu Cys
            195                 200                 205

Phe Asp Ser Leu Ala Asp Asp Val Lys Ser Leu Val Glu Lys Ser Glu
            210                 215                 220

Thr Ser Tyr Glu Glu Cys Ser Lys Asp Lys Asn Asn Pro His Cys Gly
225                 230                 235                 240

Ser Glu Gly Thr Arg Glu Leu Asp Glu Gly Leu Ile Glu Arg Glu Gln
                245                 250                 255

Lys Leu Ser Asp Cys Ile Val Glu Lys Arg Asp Ser Glu
                260                 265

<210> SEQ ID NO 6
<211> LENGTH: 807
<212> TYPE: DNA
<213> ORGANISM: Anopheles stephensi

<400> SEQUENCE: 6
atgaagcttc tactcctact agccagcgtg ctttgccttg cgctgatcgt atccgcacgg    60
ccgtccgacg agactacgga tcaagaatca tcgaccgagc taagcgaaga cacttcggat   120
agctaccacc aggaagagga tacatcagaa accggtgccg atgctggtac agaggacggt   180
aattcggaag atgactccag cgaattagaa tcttcttcgg aagaaggtca tgaggatggt   240
agcgaagacg ctactggtga ggaaggtggg gcaggcgaga aggtgaggc cggtgaggaa   300 gacgaggcag gcgaggaagg tgaggcaggt gaggaaggtg aagcaggtga agaaggtggt   360
gcaggtgaag aaggcggagc aggtgaagaa ggcggtgcag acgaagaagg tagtgcaggt   420
gaagaaggcg gtgcagaagg tggtgaagag tcccccgtta atacctacca tcaggtgcac   480
aacttgctga agaacatcat gaacgttggc acgaagaaca attacttgaa gtcgttcatt   540
ttggcccgcc tgcaggaacg tctcatgaac cccacgatcg acctggtcgg cagtatctcc   600
aaatattcca agattaagga atgcttcgac tcgctggccg acgatgtgaa atctctggtg   660
gagaagtccg aaacatcgta cgaagagtgc agcaaggaca gaataaccc tcactgcggc   720 agtgaaggta cacgcgagct tgacgaggga ctcatcgaac gggaacagaa gctatcggat   780
tgcatcgtcg aaaagcgtga ttcagag                                       807

<210> SEQ ID NO 7
<211> LENGTH: 420
<212> TYPE: PRT
<213> ORGANISM: Anopheles stephensi

<400> SEQUENCE: 7

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
                100                 105                 110

Ser Gly His Met His His His His His Ser Ser Gly Leu Val Pro
            115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Lys Ala Met
145                 150                 155                 160

Ala Ser Asp Glu Thr Thr Asp Gln Glu Ser Thr Glu Leu Ser Glu
                165                 170                 175

Asp Thr Ser Asp Ser Tyr His Gln Glu Glu Asp Thr Ser Glu Thr Gly
                180                 185                 190

Ala Asp Ala Gly Thr Glu Asp Gly Asn Ser Glu Asp Asp Ser Ser Glu
    195                 200                 205

Leu Glu Ser Ser Glu Glu Gly His Glu Asp Gly Ser Glu Asp Ala
    210                 215                 220

Thr Gly Glu Glu Gly Gly Ala Gly Glu Lys Gly Glu Ala Gly Glu Glu
225                 230                 235                 240

Asp Glu Ala Gly Glu Glu Gly Glu Ala Gly Glu Gly Glu Ala Gly
                245                 250                 255

Glu Glu Gly Gly Ala Gly Glu Gly Gly Ala Gly Glu Glu Gly Gly
                260                 265                 270

Ala Asp Glu Glu Gly Ser Ala Gly Glu Glu Gly Gly Ala Glu Gly Gly
    275                 280                 285

Glu Glu Ser Pro Val Asn Thr Tyr His Gln Val His Asn Leu Leu Lys
    290                 295                 300

Asn Ile Met Asn Val Gly Thr Lys Asn Asn Tyr Leu Lys Ser Phe Ile
305                 310                 315                 320

Leu Ala Arg Leu Gln Glu Arg Leu Met Asn Pro Thr Ile Asp Leu Val
                325                 330                 335

Gly Ser Ile Ser Lys Tyr Ser Lys Ile Lys Glu Cys Phe Asp Ser Leu
                340                 345                 350

Ala Asp Asp Val Lys Ser Leu Val Glu Lys Ser Glu Thr Ser Tyr Glu
                355                 360                 365

Glu Cys Ser Lys Asp Lys Asn Asn Pro His Cys Gly Ser Glu Gly Thr
    370                 375                 380

Arg Glu Leu Asp Glu Gly Leu Ile Glu Arg Glu Gln Lys Leu Ser Asp
385                 390                 395                 400

Cys Ile Val Glu Lys Arg Asp Ser Glu Ala Ala Ala Leu Glu His His
                405                 410                 415

His His His His
```

420

<210> SEQ ID NO 8
<211> LENGTH: 293
<212> TYPE: PRT
<213> ORGANISM: Anopheles stephensi

<400> SEQUENCE: 8

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Lys Ala Met
145                 150                 155                 160

Gly Glu Glu Ser Pro Val Asn Thr Tyr His Gln Val His Asn Leu Leu
                165                 170                 175

Lys Asn Ile Met Asn Val Gly Thr Lys Asn Asn Tyr Leu Lys Ser Phe
            180                 185                 190

Ile Leu Ala Arg Leu Gln Glu Arg Leu Met Asn Pro Thr Ile Asp Leu
        195                 200                 205

Val Gly Ser Ile Ser Lys Tyr Ser Lys Ile Lys Glu Cys Phe Asp Ser
    210                 215                 220

Leu Ala Asp Asp Val Lys Ser Leu Val Glu Lys Ser Glu Thr Ser Tyr
225                 230                 235                 240

Glu Glu Cys Ser Lys Asp Lys Asn Asn Pro His Cys Gly Ser Glu Gly
                245                 250                 255

Thr Arg Glu Leu Asp Glu Gly Leu Ile Glu Arg Glu Gln Lys Leu Ser
            260                 265                 270

Asp Cys Ile Val Glu Lys Arg Asp Ser Glu Ala Ala Leu Glu His
        275                 280                 285

His His His His His
    290

<210> SEQ ID NO 9
<211> LENGTH: 270
<212> TYPE: PRT
<213> ORGANISM: Anopheles stephensi

<400> SEQUENCE: 9

Asp Tyr Lys Asp Asp Asp Asp Lys Ile Ser Pro Ser Asp Glu Thr Thr
1               5                   10                  15

Asp Gln Glu Ser Ser Thr Glu Leu Ser Glu Asp Thr Ser Asp Ser Tyr
                20                  25                  30

His Gln Glu Glu Asp Thr Ser Glu Thr Gly Ala Asp Ala Gly Thr Glu
        35                  40                  45

Asp Gly Asn Ser Glu Asp Ser Ser Glu Leu Glu Ser Ser Ser Glu
 50                  55                  60

Glu Gly His Glu Asp Gly Ser Glu Asp Ala Thr Gly Glu Glu Gly Gly
 65                  70                  75                  80

Ala Gly Glu Lys Gly Glu Ala Gly Glu Glu Asp Glu Ala Gly Glu Glu
                85                  90                  95

Gly Glu Ala Gly Glu Glu Gly Glu Ala Gly Glu Glu Gly Gly Ala Gly
                100                 105                 110

Glu Glu Gly Gly Ala Gly Glu Gly Gly Ala Asp Glu Glu Gly Ser
        115                 120                 125

Ala Gly Glu Glu Gly Gly Ala Glu Gly Gly Glu Glu Ser Pro Val Asn
        130                 135                 140

Thr Tyr His Gln Val His Asn Leu Leu Lys Asn Ile Met Asn Val Gly
145                 150                 155                 160

Thr Lys Asn Asn Tyr Leu Lys Ser Phe Ile Leu Ala Arg Leu Gln Glu
                165                 170                 175

Arg Leu Met Asn Pro Thr Ile Asp Leu Val Gly Ser Ile Ser Lys Tyr
                180                 185                 190

Ser Lys Ile Lys Glu Cys Phe Asp Ser Leu Ala Asp Asp Val Lys Ser
            195                 200                 205

Leu Val Glu Lys Ser Glu Thr Ser Tyr Glu Glu Cys Ser Lys Asp Lys
        210                 215                 220

Asn Asn Pro His Cys Gly Ser Glu Gly Thr Arg Glu Leu Asp Glu Gly
225                 230                 235                 240

Leu Ile Glu Arg Glu Gln Lys Leu Ser Asp Cys Ile Val Glu Lys Arg
                245                 250                 255

Asp Ser Glu Ala Ala Ala Leu Glu His His His His His His
            260                 265                 270

<210> SEQ ID NO 10
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 10
gatttaggtg acactatag                                            19

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 11
taatacgact cactataggg                                           20

<210> SEQ ID NO 12
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 12

```
cttaggggc aattatggat ggta                                              24

<210> SEQ ID NO 13
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 13
caccatggcg tccgacgaga ctacggatca agaa                                  34

<210> SEQ ID NO 14
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 14
ggcggccgcc tctgaatcac gcttttcgac gatgc                                 35

<210> SEQ ID NO 15
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 15
caccatgggt gaagagtccc ccgttaatac                                       30

<210> SEQ ID NO 16
<211> LENGTH: 73
<212> TYPE: DNA
<213> ORGANISM: Artificial Sequence
<220> FEATURE:
<223> OTHER INFORMATION: Synthetic oligonucleotide primer

<400> SEQUENCE: 16
caccggatcc ggactacaag gacgacgatg acaagatcta ccgtccgacg agactacgga      60
tcaagaatca tcg                                                         73
```

PLATELET AGGREGATION INHIBITOR COMPOSITION

CROSS-REFERENCE TO RELATED APPLICATIONS

This is a divisional of U.S. patent application Ser. No. 12/065,701, filed Mar. 4, 2008 (allowed), which is a 371 National Stage Entry of International Application No. PCT/JP2006/322417, filed Nov. 2, 2006, the entire disclosures of which are incorporated by reference herein.

TECHNICAL FIELD

The present invention relates to a polypeptide having a platelet aggregation inhibitory activity and/or a platelet adhesion inhibitory activity, or a pharmaceutical composition, e.g., a platelet aggregation inhibitory composition comprising an expressed product (recombinant polypeptide), which is expressed by a polynucleotide encoding the polypeptide as an active component.

The present invention further relates to a polypeptide having a binding ability to collagen, or a pharmaceutical composition comprising the polypeptide as an active component.

The present invention also relates to a method for screening a compound (e.g., an agonist) which facilitates the platelet aggregation inhibitory activity as an active component in the pharmaceutical composition. Further, the present invention relates to a novel polypeptide having the platelet aggregation inhibitory activity and a polynucleotide encoding the same.

BACKGROUND ART

Platelets aggregate due to injury of vascular endothelial cells and other various factors. When a coronary vessel, a cerebral vessel or a peripheral vessel is occluded by this platelet thrombus, myocardial infarction, cerebral infarction or chronic artery obstruction is caused, respectively. Examples of thrombotic diseases following such an activation (stimulation of aggregation) of the platelet include arterial sclerosis, ischemic cerebral infarction, ischemic cardiac diseases including myocardial infarction and angina, chronic artery obstruction and venous thrombosis.

Medicaments with the action to inhibit the platelet aggregation are used as preventive drugs for ischemic diseases carrying with the above various diseases as complications, and
as preventive drugs for pathological conditions subsequent to hypertension, pulmonary hypertension, cerebral infarction, pulmonary infarction and subarachnoid hemorrhage. In addition, the above medicaments are used for prevention of thrombus formation upon Percutaneous transluminal coronary angioplasty (PTCA) and stent placing, and also used as preventive agents of restenosis after placing the stent by enfolding such a medicament having the action to inhibit the platelet aggregation by, applying it on or embedding it in the stent itself.

Meanwhile, a mosquito punctures skin with its sharp oral needle which reaches the peripheral blood vessel when it sucks blood, and frequently repeats a puncture-in and -out behavior referred to as probing in order to find out the peripheral blood vessel. It is believed that the mosquito simultaneously secrets saliva containing a substance to facilitate vasodilation to make the detection of the blood vessel easy. Due to the above probing, the peripheral blood vessel is often damaged to become congested. Generally, when the blood vessel is injured, collagen in tissue under vascular endothelium is exposed, adenosine diphosphate (ADP) is released from broken cells, and coagulation factors are activated to form thrombin. Thrombin strongly activates the platelet to induce platelet adhesion, the platelet aggregation and granule release, and eventually forms a firm thrombus by blood coagulation with fibrin formation (hemostasis mechanism). It has been known that the saliva of the mosquito contains the substance which inhibits such a hemostasis mechanism (see Non-patent literature 1).

A salivary gland protein in the mosquito, which has been studied in the most detail is apyrase. This enzyme is a platelet aggregation inhibiting substance which was identified in the saliva in *Aedes aegypti* for the first time. Apyrase inhibits the platelet aggregation resulting in decomposing from ADP released from damaged vascular endothelial cells, erythrocytes and adhered platelets to AMP (adenosine mono-phosphate) and to exhibit an anti-hemostatic action. To elucidate a vampire behavior of various vampire insects beyond the mosquito, it seems to be essential to analyze the function of their salivary substances.

A number of the salivary substances are predicted to be involved in inhibition of the platelet aggregation, and for example, a platelet aggregation inhibitory activity has been reported for the protein derived from *Triatoma infestans* (see Patent documents 1 and 2).

Among the proteins derived from the salivary gland in *Anopheles stephensi*, the protein having a blood coagulation inhibitory activity has been identified, but no protein having the platelet aggregation inhibitory activity has been identified (see Patent Document 3).

In addition, 33 novel proteins have been reported from cloning of cDNA library of the salivary gland in *Anopheles stephensi*, no protein having the platelet aggregation inhibitory activity is described in the report, and the functions in many of them remains to be unknown (see Non-patent literature 2).

The present inventors previously reported a protein (AAPP) having a GE (Gly Glu)-rich sequence cloned from the salivary gland in *Anopheles stephensi* (see Non-parent literature 3). The protein has an open reading frame (ORF) of 810 bases and is the protein of 28.5 kDa deduced to be composed of 269 amino acid residues. The protein was thereafter found to be similar to an antigen of 30 kDa (GenBank Accession No. AY226454) disclosed in Non-patent literature 2, but there is no description for actions and functions (activity) of the protein in Non-patent literatures 2 and 3.

[Patent Document 1] JP 2004-121091-A Publication
[Patent document 2] JP 2004-121086-A Publication
[Patent document 3] JP 2003-116573-A Publication
[Non-patent literature 1] Riberio, J. M., J. Exp. Biol., 108, 1-7(1984))
[Non-patent literature 2] Valenzuela, J. G., et. al., Exploring the salivary gland transcriptome and proteome of the *Anopheles stephensi* mosquito", Insect Biochemistry
[Non-patent literature 3] Hiroyuki Watanabe et al., Medical Entomology and Zoology 55 Suppl., pp 41, 19 (2004)

DISCLOSURE OF INVENTION

The present invention provides a novel pharmaceutical composition, particularly a platelet aggregation inhibitor and/or a platelet adhesion inhibitor.

The present invention further provides a novel pharmaceutical composition comprising a protein, which has a binding ability to collagen, as an active component.

The present invention also provides a method for screening a substance such as an agonist, the screening method which determines a platelet aggregation inhibitory activity and/or a platelet adhesion inhibitory activity of the substance.

As a result of a further extensive study separate from the study on the protein (AAPP) previously reported by the present inventors, the present inventors have found a novel protein having a platelet aggregation inhibitory activity and/or a platelet adhesion inhibitory activity in salivary gland of *Anopheles stephensi*, successfully isolated and identified a DNA encoding this, and newly found that the protein has the platelet aggregation inhibitory activity and/or a platelet adhesion inhibitory activity.

The present invention provides inventions featuring the following items 1 to 14.

Item 1. A pharmaceutical composition comprising at least one polypeptide of the following (a) to (d):
(a) a polypeptide comprising the amino acid sequence of SEQ ID NO:1;
(b) a polypeptide comprising an amino acid sequence comprising one or more amino acid deletions, insertions, substitutions or additions in the amino acid sequence of the above (a) and having a platelet aggregation inhibitory activity and/or a platelet adhesion inhibitory activity;
(c) a polypeptide comprising the amino acid sequence of SEQ ID NO:3; and
(d) a polypeptide comprising an amino acid sequence comprising one or more amino acid deletions, insertions, substitutions or additions in the amino acid sequence of the above (c) and having a platelet aggregation inhibitory activity and/or a platelet adhesion inhibitory activity,
as an active component.

Item 2. A pharmaceutical composition comprising an expressed product, which expressed by at least one polynucleotide of the following (e) to (j):
(e) a polynucleotide comprising the DNA sequence of SEQ ID NO:2 or a complement thereof;
(f) a polynucleotide which hybridizes with the polynucleotide of the above (e) under a stringent condition and is capable of expressing a polypeptide having a platelet aggregation inhibitory activity and/or a platelet adhesion inhibitory activity;
(g) a polynucleotide comprising the DNA sequence having 80% or more homology to the polynucleotide of the above (e) and capable of expressing the polypeptide having a platelet aggregation inhibitory activity and/or a platelet adhesion inhibitory activity;
(h) a polynucleotide comprising the DNA sequence of SEQ ID NO:4 or a complement thereof;
(i) a polynucleotide which hybridizes with the polynucleotide of the above (h) under the stringent condition and is capable of expressing the polypeptide having the platelet aggregation inhibitory activity and/or a platelet adhesion inhibitory activity; and
(j) a polynucleotide comprising the DNA sequence having 80% or more homology to the polynucleotide of the above (h) and capable of expressing the polypeptide having the platelet aggregation inhibitory activity and/or a platelet adhesion inhibitory activity,
as an active component.

Item 3. The pharmaceutical composition according to item 1 or 2 wherein said platelet aggregation inhibitory activity and/or a platelet adhesion inhibitory activity is the inhibitory activity to the platelet aggregation induced by collagen and/or the inhibitory activity on the platelet adhesion to collagen.

Item 4. The pharmaceutical composition according to item 1 or 2 wherein said pharmaceutical composition has the binding ability to collagen.

Item 5. A platelet aggregation inhibitor and/or platelet adhesion inhibitor, which comprising the polypeptide described in item 1 or the expressed product, which expressed by the polynucleotide described in item 2.

Item 6. A method for screening an agonist for a platelet aggregation inhibitory activity and/or a platelet adhesion inhibitory activity, wherein a level of the platelet aggregation inhibitory activity and/or a platelet adhesion inhibitory activity of the polypeptide described in item 1 is measured in the presence or absence of a subject substance and a measurement value in the presence of the subject substance is compared with a measurement value in the absence of the subject substance to select the subject substance which augments the inhibitory action as the agonist.

Item 7. A method for screening an agonist for a platelet aggregation inhibitory activity and/or a platelet adhesion inhibitory activity, wherein a level of the inhibitory activity of the expressed product, which expressed by the polynucleotide described in item 2 is measured in the presence or absence of a subject substance and a measurement value in the presence of the subject substance is compared with a measurement value in the absence of the subject substance to select the subject substance which augments the platelet aggregation inhibitory activity and/or a platelet adhesion inhibitory activity as the agonist.

Item 8. A method for screening a candidate substance which agonists a platelet inhibitory activity and/or a platelet adhesion inhibitory activity of the polypeptide described in item 1 or the expressed product described in item 2, comprising the following steps (1) to (4):
(1) a step of preparing a culture medium comprising a cell transformed with an expression vector, which express the polypeptide described in item 1 or a cell comprising the expressed product described in item 2 and platelet-rich plasma;
(2) a step of adding a platelet aggregating agent into the culture medium of the above (1) to induce the platelet aggregation in the presence or absence of a subject substance;
(3) a step of measuring a level of the platelet aggregation in the presence or absence of the subject substance in the above (2); and
(4) a step of selecting the subject substance as the candidate substance when a measurement value in the presence of the subject substance is larger than a measurement value in the absence of the subject substance.

Item 9. A kit for screening an agonist for the polypeptide described in item 1 or the expressed product expressed by the polynucleotide described in item 2, characterized by containing platelet-rich plasma, either one of the polypeptide described in item 1 and the expressed product described in item 2, and a platelet aggregating agent as components.

Item 10. An isolated polypeptide comprising the amino acid sequence of SEQ ID NO:1.

Item 11. An isolated polypeptide comprising the amino acid sequence of SEQ ID NO:3.

Item 12. An isolated polypeptide comprising the amino acid sequence of SEQ ID NO:5.

Item 13. A polynucleotide comprising the DNA sequence of SEQ ID NO:2 or a complement thereof.

Item 14. A polynucleotide comprising the DNA sequence of SEQ ID NO:4 or a complement thereof.

Item 15. A polynucleotide comprising the DNA sequence of SEQ ID NO:6 or a complement thereof.

At least one polypeptide (protein) of the above (a) to (d) is sometimes referred to as "SY-001" hereinafter. The expressed product by at least one polynucleotide of the above (e) to (j) is sometimes referred to as the "expressed product of the present invention".

BEST MODES FOR CARRYING OUT THE INVENTION

Figure 1:
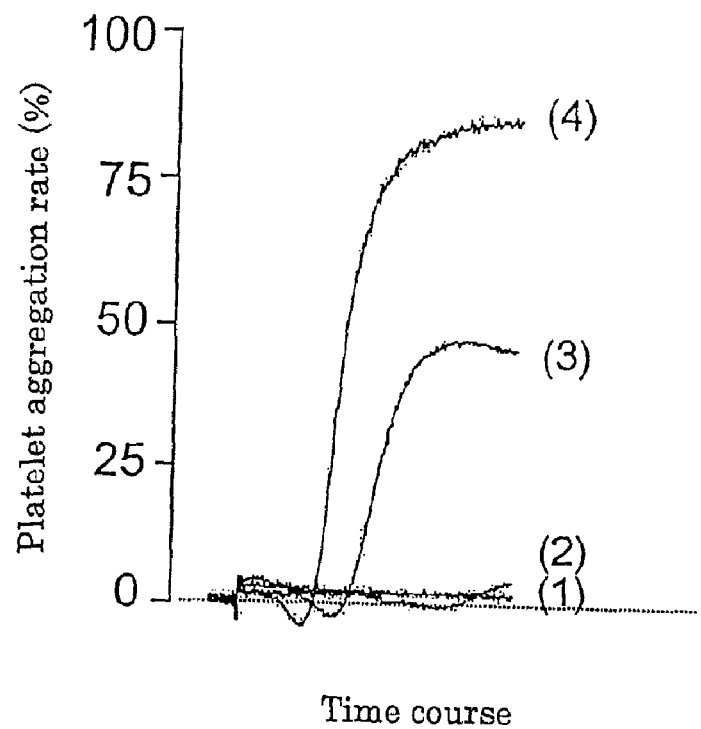
FIG. 1 shows the platelet aggregation inhibitory activity of SY-001 produced in Example 1, 3(1) induced by stimulation with collagen.

Representation herein by abbreviations of amino acids, peptides, base sequences and nucleic acids accedes to IUPAC-IUB Communication on Biological Nomenclature, Eur. J. Biochem., 138: 9(1984) defined by IUPAC-IUB, "Guideline for preparing specifications comprising base sequences and amino acid sequences" (Patent Office) and commonly used notes in the art.

A polynucleotide (DNA molecule) herein encompasses not only double strand DNA but also single strand DNA including sense chains and antisense chains which compose them, and is not limited to a length thereof. Therefore, the polynucleotide encoding SY-001 includes the double strand DNA including genomic DNA and the single strand DNA (sense chain) including cDNA and the single strand DNA (antisense chain) having the sequence complementary to the sense chain and synthetic DNA fragments thereof unless otherwise mentioned.

The polynucleotide (DNA molecule) herein is not defined by a functional region, and can include at least one of an expression suppression region, a coding region, a leader sequence, an exon and an intron.

The polynucleotide also includes RNA and DNA. The polypeptide comprising the certain amino acid sequence and the polynucleotide comprising the certain DNA sequence include fragments, homologs, derivatives and mutants thereof.

The mutants of the polynucleotide (mutant DNA) include naturally occurring allelic mutants, not naturally occurring mutants and mutants having deletion, substitution, addition and insertion. But, these mutants encode the polypeptide having substantially the same function as the function of the polypeptide encoded by the polynucleotide before the mutation.

The mutation of the polypeptide (modification of amino acid sequence) is not necessary to occur by the naturally occurring one, e.g., mutation or posttranslational modification, and may be those artificially made by utilizing the naturally occurring protein (e.g., SY-001). The above mutants of the polypeptide include allelic variants, homologs and natural mutants having at least 80%, preferably 95% and more preferably 99% homology to the polypeptide before the mutation.

The homology of the polypeptide or the polynucleotide can be analyzed by measurement using FASTA program (Clustal, V., Methods Mol. Biol., 25, 307-318 (1994)). As the most preferable and simple method for homology analysis, it is possible to exemplify the method in which the sequence is stored on a medium (e.g., flexible disc, CD-ROM, hard disc drive, external disc drive, DVD, etc.) capable of being read by computer and then known sequence database is searched in accordance with well-known searching procedure using the stored sequence. Specific examples of the known sequence database include the followings:

DNA Database of Japan (DDBJ) (www.ddbj.nig.ac.jp/);
Genebank (www.ncbi.nlm.nih.gov/web/Genebank/Index.htlm); and
the European Molecular Biology Laboratory Nucleic Acid Sequence Database (EMBL) (www.ebi.ac.uk/ebi docs/embl db.html).

Lots of searching algorithms for the homology analysis are available for those skilled in the art. One example thereof includes a program referred to as BLAST program. There are 5 BLAST procedures in this program. Three (BLASTN, BLASTX and TBLASTX) among them have been designed for checking the nucleotide sequence. Remaining two have been designed for checking the protein sequence (Coulson, Trends in Biotechnology, 12:76-80 (1994); Birren, et al., Genome Analysis, 1:543-559(1997)).

In addition, additional programs, e.g., a sequence alignment program and a program for identifying the sequences more distantly separated are available in the art for analyzing the identified sequence.

The mutant DNA is silent (no change in an amino acid residue encoded by a mutated nucleic acid sequence) or conservative for the amino acid encoded by this. Examples of conservative amino acid substitution are shown below.

| Original amino acid residue | Conservative substituted amino acid residue |
|---|---|
| Ala | Ser |
| Arg | Lys |
| Asn | Gln or His |
| Asp | Glu |
| Cys | Ser |
| Gln | Asn |
| Glu | Asp |
| Gly | Pro |
| His | Asn or Gln |
| Ile | Leu or Val |
| Leu | Ile or Val |
| Lys | Arg, Asn or Glu |
| Met | Leu or Ile |
| Phe | Met, Leu or Tyr |
| Ser | Thr |
| Thr | Ser |
| Trp | Tyr |
| Tyr | Trp or Phe |
| Val | Ile or Leu |

Generally, one or more codons encoding a Cys residue affects a disulfide bond of the particular polypeptide.

The substitution of the amino acid residue generally thought to affect characteristics of the protein includes the followings:

a) the substitution of a hydrophobic residue with a hydrophilic residue, e.g., the substitution of Leu, Ile, Phe Val or Ala with Ser or Thr;
b) the substitution of the amino acid residue other than Cys and Pro with Cys or Pro;
c) the substitution of the residue having an electrically positive side chain, e.g., Lys, Arg or His with an electrically negative residue, e.g., Glu or Asp; and
d) the substitution of the amino acid residue having an extremely large side chain, e.g., Phe with the amino acid residue having no side chain, e.g., Gly.

(1) SY-001

SY-001 comprises the amino acid sequence of SEQ ID NO:1 or 3 or the amino acid sequence having one or more amino acid deletions, insertions, substitutions or additions in the amino acid sequence of SEQ ID NO:1 or 3, and has the platelet aggregation inhibitory activity and/or the platelet adhesion inhibitory activity, which inhibits the platelet adhesion to collagen and/or the binding ability to collagen.

SY-001 may be the polypeptide expressed in a protein expression system using Escherichia coli or a protein expression system using baculovirus (AcNPV) shown in Examples described later by gene recombination technology or the polypeptide obtained by chemically synthesizing.

As one specific example of the amino acid sequence of SY-001, it is possible to exemplify one of SEQ ID NO:1 or 3. The amino acid sequence of SY-001 is not limited to one of SEQ ID NO:1 or 3, and can be those (homologous ones) having a certain homology thereto. The homologous ones can include the polypeptides comprising the amino acid sequence having one or more amino acid deletions, insertions, substitutions or additions in the amino acid sequence of SEQ ID NO:1 or 3 and having the platelet aggregation inhibitory activity and/or the platelet adhesion inhibitory activity, which inhibits the platelet adhesion to collagen and/or the binding ability to collagen.

The platelet aggregation inhibitory activity, which SY-001 has include actions to inhibit or block the condition in which the substance which induces the platelet aggregation increases in human blood vessel (particularly in coronary artery, aorta and cerebral artery) or an aggregation ability of platelets is facilitated in the blood vessel, or the condition in which the damage has occurred in the blood vessel and the platelets excessively aggregates at the damaged site.

This platelet aggregation inhibitory activity can be detected by inhibiting (suppressing) the aggregation of the platelets induced by the platelet aggregating agent in the platelet-rich plasma (PRP) by adding SY-001 into the plasma in the experiment in vitro.

More particularly, the platelet aggregation inhibitory activity of SY-001 can be determined by the following method. That is, first, the PRP is prepared from human whole blood by centrifugation. Subsequently, this prepared PRP is preincubated with a solution, e.g., PBS solution containing SY-001, and the platelet aggregating agent is further added to this solution to aggregate the platelets. Examples of the platelet aggregating agent include ADP (adenosine di-phosphate), collagen, CRP (collagen related peptide), convulxin, TRAP (thrombin receptor activator peptide), epinephrine, arachidonic acid, U-46619 (thromboxane A2 analog, TXA2 analog) and A23187 (calcium ionophore). A platelet aggregation rate of the resulting solution is measured using a turbidimetric light-transmittance platelet aggregometer (MCM HEMA TRACER 313M: supplied from MC Medical), and a platelet aggregation inhibitory rate of SY-001 is calculated from an obtained measurement value based on the value in the control containing no SY-001. Thus, the platelet aggregation inhibitory activity of SY-001 can be detected.

The platelet adhesion inhibitory activity of SY-001 can be also determined by the following method.

PBS solution containing SY-001 at given concentrations is added to 96 well plate coated with collagen solution and is incubated for 30 minutes at room temperature. After the incubation, the platelet suspension is added to well and is incubated for 45 minutes at room temperature. After the incubation, the incubation solution is removed with pipette from well and the well is washed with PBS.

PBS solution containing 1% SDS is added to well, and the well is dried with air after the shaking and the stirring. Then, the distilled water is added to well, the amount of protein in each well is measured using a Dc protein assay kit (BIO-RAD Laboratories). The platelet adhesion inhibitory activity rate of SY-001 is calculated from an obtained measurement value based on the value in the control containing no SY-001 and calculating the platelet adhesion inhibitory activity of SY-001 from its platelet adhesion curve. Thus, the platelet adhesion inhibitory activity of SY-001, which inhibits the platelet adhesion to collagen can be detected.

The collagen binding ability of SY-001 can be also determined by the following method.

A 300 µl blocking solution is added to each 96 well plate with or without a collagen coating and is incubated for 1 hour. After removing the incubation solution from each well, 100 µl of the solution containing SY-001 at given concentrations is added to each well and is incubated for 1 hour at room temperature. After removing the incubation solution from each well, 200 µl of the 2% sucrose is then added to each well and is incubated for 5 minutes at room temperature. After removing the incubation solution from each well and the wells are dried, 100 µl of the reconstituted Ni-HRP solution (KPP: Kirkegaard & Perry Laborator, Ltd.) is added to each well and is incubated for 30 minutes at room temperature. After washing with wash buffer, 100 µl of ABTS Peroxidase Substrate (KPL Ltd.) is added to each well, and the 96 well plate is gently shaken, After finishing the reaction, 100 µl of 1% SDS is added to each well, and the well is then measured using a Micro Plate Reader with an absorbance change at 405-410 nm.

The collagen binding ability of SY-001 at given concentrations is calculated from an obtained OD value based on the value in the control vector containing no SY-001 and calculating the collagen binding ability of SY-001 from its collagen binding curve. Thus, the collagen binding ability of SY-001 can be detected.

An anti-platelet activity which SY-001 has can also be determined by the following method. That is, PRP is prepared from the whole blood obtained by collecting a blood sample using a syringe with an anticoagulant from a healthy donor by centrifugation. Then, the prepared PRP is diluted with an appropriate buffer, e.g., Tyrode-Hepes (134 mM NaCl, 0.34 mM $Na_2HPO_4$, 2.9 mM KCl, 12 mM $NaHCO_3$, 20 mM Hepes, 5 mM glucose, 1 mM $MgCl_2$, pH 7.3), and SY-001 at given concentrations is added to this serial dilution and pre-incubated.

Fluorescence-labeled anti-P selectin antibody, an antibody (supplied from Becton Dickinson) which recognizes PAC-1 (GPIIb/GPIIIa complex), fibrinogen and annexin V are added to this solution, and subsequently the platelet aggregating agent, e.g., ADP, collagen or TRAP is added to activate the platelets. Thus, fluorescent intensity of the activated platelets is measured by flow cytometry to evaluate the activity (inhibitory activity on activation) of SY-001 on the platelet activation. This inhibitory activity on the platelet activation is a platelet activation inhibitory activity.

In the above method, if fluorescence labeled antibodies which recognize the platelet and the leukocyte are used, it is also possible to evaluate the action of the compound on an interaction of the platelet and the leukocyte (platelet-leukocyte adhesion).

For details of the method for measuring the inhibitory activity of SY-001 on the platelet aggregation utilizing the turbidimetric light-transmittance platelet aggregometer, the present invention makes reference to, for example, Born, G. V. R., "Aggregation of blood platelets by adenosine diphosphate and its reversal", Nature, 1962, 194, 927-9 and Sudo, T., et al., "Potent effects of novel anti-platelet aggregatory cilostamide analogues on recombinant cyclic nucleotide phosphodiesterase isozyme activity", Biochem. Pharmacol., 2000, 59, 347-56. For the measurement of the platelet activation, the present invention also makes reference to, for example, Ito, H., et al., "Cilostazol inhibits platelet-leukocyte interaction by suppression of platelet activation", Platelets, 2004, 15, 293-301.

Therefore, SY-001 having the inhibitory activity on the platelet aggregation and/or the inhibitory activity on the platelet adhesion has a possibility as a therapeutic agent for occurrence or prevention of blood related diseases and complications thereof by acting upon the blood and the blood vessel in mammalian animals to inhibit or prevent the formation of thrombus or embolus.

Accordingly, SY-001 having the inhibitory activity on the platelet aggregation and/or the inhibitory activity on the platelet adhesion has a possibility is thought to be useful as the therapeutic agent or the preventive agent for the pathological conditions subsequent to the diseases and the complications thereof, e.g., myocardial infarction, cerebral embolism, chronic arterial obstruction, arterial sclerosis, ischemic cerebral infarction, angina, venous thrombosis, hypertension, pulmonary hypertension, cerebral infarction, pulmonary infarction, cardiac failure, nephritis, renal failure and subarachnoid hemorrhage, caused by the formation of thrombus or embolus.

SY-001 having the inhibitory activity on the platelet aggregation and/or the inhibitory activity on the platelet adhesion has a possibility is also thought to be useful for the prevention of the thrombus formation upon PTCA and stent placing and as the preventive agent of restenosis after placing the stent by enfolding the medicament containing SY-001 by, applying it on or embedding it in the stent itself.

A degree and a position of the modification, i.e., the "deletion, insertion, substitution or addition" of the amino acid residues in SY-001 represented as the above (b) and (d) are not particularly limited as long as the polypeptide (equivalent one) comprising the modified amino acid sequence has substantially the same activity as that of the polypeptide comprising the amino acid sequence of SEQ ID NO:1 or 3. It is preferable that the above modification is typically performed at about one to several amino acid residues.

In the present invention, the "deletions, insertions, substitutions or additions of multiple amino acids" refer to that 2 or more and 20 or less of amino acids have been deleted, inserted, substituted or added. The multiple amino acids are preferably 2 or more and 10 or less, more preferably 2 or more and 7 or less and still more preferably 2 or more and 5 or less. This modified amino acid sequence has, for example, about 70% or more, preferably about 80% or more, more preferably about 95% or more and still more preferably about 98% or more homology to the amino acid sequence of either SEQ ID NO:1 or 3.

Specific examples of the polypeptide (SY-001) which is the active component of the pharmaceutical composition of the present invention are as shown in Examples described later.

SY-001 has the inherent platelet aggregation inhibitory activity and/or the platelet adhesion inhibitory activity.

SY-001 also has the inherent collagen binding ability.

Therefore, the pharmaceutical composition of the present invention containing SY-001 as the active component is useful as the therapeutic agent or the preventive agent for the pathological condition subsequent to the diseases and the complications thereof, e.g., acute coronary syndrome, myocardial infarction, cerebral embolism, chronic arterial obstruction, arterial sclerosis, ischemic cerebral infarction, angina, venous thrombosis, hypertension, pulmonary hypertension, cerebral infarction, pulmonary infarction, cardiac failure, nephritis, renal failure and subarachnoid hemorrhage, caused by the formation of thrombus or embolus. The pharmaceutical composition of the present invention is also useful for the prevention of the thrombus formation upon PTCA and stent placing and as the preventive agent of restenosis after placing the stent by applying this on the stent itself.

(2) Polynucleotide (DNA Molecule) Encoding SY-001

One specific example of the polynucleotide encoding SY-001 (sometimes referred to as a "DNA molecule of SY-001") can include the polynucleotide (DNA molecule) comprising the DNA sequence of SEQ ID NO:2 or 4 or the complement thereof.

Another example of the DNA molecule of SY-001 includes the polynucleotide which hybridize with the polynucleotide comprising the complement to the DNA sequence of SEQ ID NO:2 or 4 under the stringent condition and is capable of expressing the polypeptide having the platelet aggregation inhibitory activity and/or the platelet adhesion inhibitory activity.

The "stringent condition" herein can include the condition in which the hybridization occurs in 2×SSC containing 0.1% SDS at 50° C. and is not separated by washing in 1×SSC containing 0.1% SDS at 60° C.

Furthermore, another example of the DNA molecule (polynucleotide) of SY-001 includes the polynucleotide comprising the DNA sequence having 80% or more, preferably 95% or more and more preferably about 98% or more homology to the most closely related one among the polynucleotides comprising the DNA sequence of SEQ ID NO:2 or 4 or the complement thereof and capable of expressing the polypeptide having the platelet aggregation inhibitory activity and/or the platelet adhesion inhibitory activity.

For the DNA molecules (sometimes referred to as modified DNA molecules) capable of expressing the polypeptides shown as these other examples having the desired action, it is an essential requirement that the polypeptide of the amino acid sequence encoded by the DNA molecule can express the platelet aggregation inhibitory activity and/or the platelet adhesion inhibitory activity (particularly, the inhibitory activity on the platelet aggregation induced by collagen and/or the inhibitory activity on the platelet adhesion to collagen). In other words, the requirement is that a transformant transformed with a recombinant expression vector in which the polynucleotide (modified DNA molecule) has been inserted can express the protein having the platelet aggregation inhibitory activity and/or the platelet adhesion inhibitory activity as the expressed product thereof.

The above modified DNA molecule includes DNA molecules including the DNA sequences encoding the amino acid sequence of SEQ ID NO:1 or 3, particularly the amino acid sequences (modified amino acid sequences) having one or more amino acid deletions, insertions, substitutions or additions and the DNA sequences encoding the complement thereof. The modified DNA may be those which can detect the DNA molecule of the present invention before the modification by utilizing it.

A homologous DNA molecule to the polynucleotide (DNA of SY-001 or fragments thereof) included in the DNA molecule of SY-001 and comprising the DNA sequence of SEQ ID NO:2 or 4 means a series of related DNA molecules having sequence homology to the DNA sequence of SEQ ID NO:2 or 4 and recognized as one DNA molecule family by their structural characteristics, and commonality in their expression patterns and similarity in their biological functions.

Such a homologous DNA molecule may be those artificially made based on the naturally occurring DNA molecule (e.g., DNA fragment of SY-001). Examples of this artificial procedure include gene engineering techniques such as site-specific mutagenesis [Methods in Enzymology, 154, 350, 367-382(1987); ibid. 100, 468(1983); Nucleic Acids Res., 12, 9441(1984)); "Zoku Seikagaku Jikken Kouza 1", "Idenshi Kenkyuho II" edited by the Japanese Biochemical Society, p 105 (1986)], chemical synthesis procedures such as phosphotriester method and phosphoamidite method [J. Am. Chem. Soc., 89, 4801 (1967); ibid. 91, 3350 (1969); Science, 150, 178 (1968); Tetrahedron Lett., 22, 1859 (1981); ibid. 24, 245 (1983)] and combinations thereof. More specifically, the DNA molecule can also be synthesized by phosphoramidite method or phosphotriester method, and can also be synthesized using a commercially available automatic oligonucleotide synthesizer. A double strand fragment can be obtained by synthesizing a complementary chain and annealing the complementary chain with a chemically synthesized single strand chain under an appropriate condition or adding the complementary chain to the chemically synthesized single strand chain using DNA polymerase with appropriate primers.

The DNA sequence of SEQ ID NO:2 or 4 which is one specific embodiment of the DNA molecule of SY-001 is one combination example of codons encoding amino acid residues of the polypeptide comprising the amino acid sequence of SEQ ID NO:1 or 3. The DNA molecule of SY-001 is not limited to the DNA molecule having such a particular DNA sequence, and can have the combination of optional codons and the selected DNA sequence for each amino acid residue. The codon can be selected in accordance with the standard method. At that time, a codon usage frequency in a host used can be considered [Nucleic Acids Res., 9, 43 (1981)].

(3) Production of DNA Molecule of SY-001

The DNA molecule of SY-001 can be easily produced and obtained by synthesizing based on the nucleic acid sequence information of the polynucleotide encoding SY-001 disclosed herein or directly synthesizing the DNA molecule corresponding to the nucleic acid sequence encoding the amino acid sequence based on the amino acid sequence information of SY-001 (chemical DNA synthesis). General gene engineering techniques can be applied to this production [e.g., see Molecular Cloning 2d Ed, Cold Spring Harbor Lab. Press (1989); "Zoku Seikagaku Jikken Kouza 1", "Idenshi Kenkyuho II" edited by the Japanese Biochemical Society (1986)].

As a chemical DNA synthesis method in which the DNA molecule of SY-001 is directly synthesized, it is possible to exemplify a solid phase synthesis method by a phosphoamidite method. An automatic synthesizer can be used for this synthesis method.

The production of the DNA molecule of SY-001 by the gene engineering technique can more specifically be carried out by preparing a cDNA library from an appropriate source in which the DNA molecule of SY-001 has been expressed in accordance with the standard method and selecting a desired clone from the library using an appropriate probe or antibody specific for the DNA molecule of SY-001 [Proc. Natl. Acad. Sci., USA., 78, 6613 (1981); Science, 222, 778 (1983)].

In the above, as the source of the cDNA, it is possible to exemplify various cells and tissues in which the DNA molecule of SY-001 is expressed and cultured cells derived therefrom. In particular, it is desirable to make the salivary gland of Anopheles stephensi which is an assassin bug the source. All of the extraction and isolation of total RNA from the source, the separation and purification of mRNA, and the acquisition and cloning of cDNA can be carried out in accordance with the standard methods.

The DNA molecule of SY-001 can be produced using the salivary gland cDNA library of Anopheles stephensi obtained by extracting, separating and purifying the salivary gland mRNA. In addition to this, the DNA molecule of SY-001 can also be produced using a phage library prepared by extracting the above salivary gland mRNA, adding poly A to the RNA, then collecting the RNA with poly A, producing cDNA using reverse transcriptase, and subsequently adding restriction enzyme sites at both ends of the cDNA, which is incorporated in a phage.

The method for screening the DNA molecule of SY-001 from the cDNA library is not particularly limited, and can be performed in accordance with the standard methods. As the specific method, it is possible to exemplify the method in which a corresponding cDNA clone is selected by immunological screening using an antibody (e.g., anti-Anopheles stephensi saliva antibody) specific for the protein produced by the cDNA, a plaque hybridization method using the probe which is selectively bound to the objective DNA sequence, a colony hybridization method, and combinations thereof.

The probe used in each hybridization method above is generally the DNA fragment chemically synthesized based on the information for the DNA sequence of the DNA molecule of SY-001. The DNA molecule of SY-001 and the fragment thereof already obtained can be advantageously utilized as the above probe. Furthermore, a sense primer and an antisense primer obtained based on the DNA sequence information for the DNA molecule of SY-001 can also be used as the probes for the above screening.

The DNA (nucleotides) used as the probe is the partial DNA (nucleotides) corresponding to the DNA sequence of SY-001 and comprises at least 15 consecutive DNA, preferably at least 20 consecutive DNA and more preferably at least 30 consecutive DNA. The positive clone itself for the above production of the DNA molecule of the present invention can be used as the probe.

When the DNA molecule of SY-001 is obtained, an amplification method of DNA/RNA by PCR method [Science, 230, 1350 (1985)] can be suitably used. In particular, when it is difficult to obtain full length cDNA from the library, RACE method [Rapid amplification of cDNA ends; Jikken Igaku, 12 (6), 35 (1994)], particularly 5'-RACE method [M. A. Frohman, et al., Proc. Natl. Acad. Sci., USA., 8, 8998 (1988)] may be employed suitably.

The primer used for the PCR method can be optionally designed based on the sequence information of the DNA molecule of SY-001 demonstrated in Example described later, and synthesized in accordance with the standard method. As this primer, it is also possible to use DNA portions (SP6 promoter primer and T7 terminator primer) added at both ends of cDNA of a vector plasmid in which the cDNA of SY-001 has been incorporated as shown in Example described later.

The DNA/RNA fragment amplified by the PCR method can be isolated and purified in accordance with the standard methods, e.g., a gel electrophoresis method.

The DNA molecule of SY-001 and various DNA fragments thereof obtained as the above can be sequenced in accordance with the standard method, e.g., a dideoxy method [Proc. Natl. Acad. Sci., USA., 74, 5463 (1977)] or a Maxam-Gilbert method [Methods in Enzymology, 65, 499(1980)] or simply using a commercially available sequencing kit.

(4) Genetically Engineered Production of Expressed Product of the Present Invention The expressed product (recombinant SY-001) of the present invention can be easily and stably produced in a large amount as the expressed product of the DNA molecule or the protein containing this using the sequence information of the DNA molecule of SY-001 in accordance with common gene engineering techniques [e.g., Science, 224, 1431 (1984); Biochem. Biophys. Res. Comm., 130, 692(1985); Proc. Natl. Acad. Sci., USA., 80, 5990 (1983)]. More particularly, the expressed product of the present invention can be obtained by preparing a recombinant DNA (expression vector) capable of expressing the DNA encoding the desired protein in a host cell, transforming the host cell with this vector to obtain a transformant, culturing the transformant and collecting the objective protein from the resulting culture.

In the production of the expressed product of the present invention, any of prokaryotic organisms and eukaryotic organisms can be used as the host cell. For example, the prokaryotic organism as the host may be any of *Escherichia coli*, *Bacillus subtilis* and the like generally used. Suitably, *Escherichia coli*, particularly *Escherichia coli* K12 strain can be used. The host cells of the eukaryotic organisms include cells from vertebrates and yeast. The former examples suitably include COS cells from monkey [Cell, 23: 175 (1981)], ovarian cells from Chinese hamster and a dihydrofolic acid reductase deletion line thereof [Proc. Natl. Acad. Sci., USA., 77: 4216 (1980)], and the latter examples suitably include yeast cells belonging to genus *Saccharomyces*. The host cells are not of course limited thereto.

When the prokaryotic cell is used as the host, using a vector capable of replicating in the host cell, it is possible to suitably use an expression plasmid obtained by incorporating a promoter and SD (Shain and Dalgarano) sequence and an initiation codon (e.g., ATG) required for the initiation of protein synthesis at upstream of the gene of the present invention so that the gene can be expressed in this vector. As the above vector, generally the plasmids such as pET-16b, pET-32, pBR322, pBR325, pUC12 and pUC13 derived from *Escherichia coli* are often used. Without being limited thereto, known various vectors can be utilized. Examples of the commercially available vector used for an expression system using *Escherichia coli* include pGEX-4T (Amersham Pharmacia Biotech), pMAL-C2, pMAL-P2 (New England Biolabs), pET-16, pET-32, pET-21, pET-21/lacq (Invitrogen) and pBAD/His (Invitrogen).

The expression vector when a vertebrate cell is used as the host include those typically having the promoter, a splicing site of RNA, a polyadenylation site and a transcription termination sequence located at the upstream of the gene of the present invention to be expressed. These may further have an origin of replication if necessary. Specifically, examples of the expression vector include pSV2dhfr [Mol. Cell. Biol., 1: 854 (1981)] having an early promoter of SV40. In addition to the above, commercially available known various vectors can be used. Examples of the commercially available vectors used for the expression system using the animal cell include the vectors such as pEGFP-N, pEGFP-C (Clontrech), pIND (Invitrogen) and pcDNA3.1/His (Invitrogen) for the animal cells and the vectors such as pFastBac HT (GibciBRL), pAcGHLT (PharMingen), pAc5/V5-His, pMT/V5-His and pMT/Bip/V5-his (Invitrogen) for insect cells.

As the vector for the insect cell, it is possible to exemplify a baculovirus vector (Takara) in which cDNA of SY-001 has been incorporated. Specifically, the expressed product of the present invention can be obtained by introducing the baculovirus expression vector in which cDNA of SY-001 has been incorporated into cultured cells BmN4 or larvae of silkworm (*Bombyx mori*) using nuclear polyhedrosis virus (BmNPV) of silkworm to express, and isolating from a culture medium or a silkworm body fluid by chromatography. The expressed product of the present invention can also be obtained by incorporating the cDNA of SY-001 into the nuclear polyhedrosis virus (AcNPV) of *Autographa californica*, expressing it in Sf9 cells of *Spodoptera frugiperda* or Tn5 cells of *Trichoplusia ni*, and likewise purifying from a culture supernatant by chromatography.

Specific examples of the expression vector when the yeast cell is used as the host include pAM82 [Proc. Natl. Acad. Sci., USA., 80: 1 (1983)] having the promoter for acid phosphatase gene. Examples of the commercially available expression vector for the yeast cell include pPICZ (Invitrogen) and pPICZα (Invitrogen).

The promoter is not particularly limited. When a bacterium belonging to genus *Escherichia* is used as the host, it is possible to preferably use tryptophan (trp) promoter, 1pp promoter, lac promoter, recA promoter and PL/PR promoter. When the host belongs to genus *Bacillus*, SP01 promoter, SP02 promoter, penP promoter and the like are preferable. When the yeast is used as the host, it is possible to suitably use pH05 promoter, PGK promoter, GAP promoter, ADH promoter and the like. The preferable promoters when the animal cell is used as the host are the promoter derived from SV40, the promoter of retrovirus, metallothionein promoter, heat shock promoter, cytomegalovirus promoter, SRα promoter and the like. When the insect cell is used as the host, it is possible to exemplify p10 baculovirus promoter, polyhedrin promoter and the like.

As the expression vector of the DNA molecule of SY-001, an expression vector for a fusion protein can be preferably used. Specific examples of the vector include pGEX (Promega) for expressing as the fusion protein with glutathion-S-transferase (GST).

As the polynucleotide sequence corresponding to a coding sequence in the mature polypeptide, which helps the expression and the secretion of the polypeptide from the host cell, it is possible to exemplify a secretory sequence and a leader sequence. These sequences include marker sequences (hexahistidine tag, histidine tag), e.g., hemagglutinin tag in the case of the animal cell, used for the purification of the fused mature polypeptide in the bacterial host.

The method for introducing the desired recombinant DNA (expression vector) into the host cell and the method for transforming with this are not particularly limited, and various general methods can be employed.

The resulting transformant can be cultured in accordance with the standard methods, and by the culture, the objective protein (expressed product) encoded by the DNA molecule of SY-001 designed as desired is expressed and produced (accumulated and secreted) intracellularly or extracellularly or on a cell membrane in the transformant.

As a medium used for the culture, various media commonly used can be optionally selected and used depending on the host cell employed. The culture can also be carried out under the condition suitable for growth of the host cell.

The expressed product (recombinant protein) of the present invention obtained in this way can be separated and purified by various separation manipulations [see Biochemistry Data Book II, pages 1175-1259, 1st edition 1st printing published by Tokyo Kagaku Dojin on Jun. 23, 1980; Biochemistry, 25 (25), 8274 (1986); Eur. J. Biochem., 163, 313 (1987)] utilizing its physical and chemical natures as desired.

Such methods specifically include usual treatment of rearrangement, treatment (salting out) by a protein precipitating agent, centrifugation, osmotic shock, sonication, ultrafiltration, various liquid chromatography such as molecular sieve chromatography (gel filtration), absorption chromatography, ion-exchange chromatography, affinity chromatography and high performance liquid chromatography (HPLC), dialysis and combinations thereof. The particularly preferable method includes the affinity chromatography using a column to which the antibody specific for SY-001 has been bound.

When the polynucleotide encoding SY-001 is designed, it is possible to use the DNA sequence of the DNA molecule of SY-001 of SEQ ID NO:2. In the sequence, it is also possible to optionally select, change and use the codon for each amino acid residue as desired.

In the amino acid sequence of SY-001, when a part of the amino acid residues or the amino acid sequence is modified by substitution, insertion, deletion or addition, various methods such as site-specific mutagenesis described above can be employed.

(5) Expressed Product of the Present Invention Which is Active Component of Pharmaceutical Composition of the Present Invention The expressed product (and the same expressed product used for the screening method of the present invention) of the present invention which is the active component of the pharmaceutical composition of the present invention can be obtained by the gene engineering techniques shown in the above (4).

The inhibitory activity of the expressed product of the present invention on the platelet aggregation is the same as defined for the platelet aggregation inhibitory activity of SY-001 described in the above (1). This inhibitory activity can be determined in accordance with the platelet aggregation test method publicly known, e.g., by the aggregation determination method of the platelet-rich plasma (PRP) using the turbidimetric light-transmittance platelet aggregometer.

More particularly, the platelet aggregation inhibitory activity of the expressed product of the present invention on the platelet aggregation can be determined and evaluated by measuring the level of the platelet aggregation by the addition of the platelet aggregating agent in PRP prepared from the human blood in the presence or absence of SY-001 using the turbidimetric light-transmittance platelet aggregometer, and calculating the platelet aggregation inhibitory rate of SY-001 from its platelet aggregation curve.

The inhibitory activity of the expressed product of the present invention on the platelet adhesion is the same as defined for the platelet adhesion inhibitory activity (i.e. inhibit the platelet adhesion to collagen) of SY-001 described in the above (1). This inhibitory activity can be determined in accordance with the test method of the platelet adhesion to collagen publicly known, e.g., by the determination method of the platelet adhesion to collagen using the Dc protein assay kit (BIO-RAD Laboratories).

More particularly, the platelet adhesion inhibitory activity of the expressed product of the present invention on the platelet adhesion to collagen can be determined and evaluated by measuring the level of the platelet adhesion to collagen by the addition of the platelet suspension prepared from the human blood in the presence or absence of SY-001 using the Dc protein assay kit, and calculating the platelet adhesion inhibitory activity of SY-001 from its platelet adhesion curve.

The collagen binding ability of the expressed product of the present invention on the collagen binding is the same as defined for the collagen binding ability (i.e. SY-001 binds to collagen) of SY-001 described in the above (1). This collagen binding ability can be determined in accordance with the test method of the collagen binding publicly known, e.g., by the determination method of the collagen binding ability using a Micro Plate Reader with an absorbance change at 405-410 nm.

More particularly, the collagen binding ability of the expressed product of the present invention on the collagen binding can be determined and evaluated by measuring the level of the collagen binding ability of SY-001 by the addition of SY-001 at given concentrations in the presence or absence of collagen using the microplate reader with an absorbance change at 405-410 nm, and calculating the collagen binding ability of SY-001 from its collagen binding curve.

The composition of the present invention is useful as the therapeutic agent or the preventive agent for the pathological conditions subsequent to the diseases and the complications thereof, e.g., acute coronary syndrome, myocardial infarction, cerebral embolism, chronic arterial obstruction, arterial sclerosis, ischemic cerebral infarction, angina, venous thrombosis, hypertension, pulmonary hypertension, cerebral infarction, pulmonary infarction, cardiac failure, nephritis, renal failure and subarachnoid hemorrhage, caused by the formation of thrombus or embolus, by the inhibitory activity of the expressed product of the present invention on the platelet aggregation and/or the platelet adhesion based on comprising the expressed product of the present invention as the active component. The composition of the present invention is also useful for the prevention of the thrombus formation upon PTCA and stent placing and as the preventive agent of restenosis after placing the stent by enfolding this by, applying this on or embedding this in the stent itself.

(6) Chemical Synthesis of SY-001 Which is Active Component of Pharmaceutical Composition of the Present Invention.

The polypeptide (SY-001) which is the active component of the pharmaceutical composition of the present invention can also be produced by the general chemical synthesis method in accordance with the amino acid sequence information of SEQ ID NO:1 or 3. The method includes peptide synthesis methods by a usual liquid phase method or solid phase method. The peptide synthesis methods include a so-called stepwise elongation method in which each amino acid is sequentially synthesized and bound one by one to elongate the chain and a fragment condensation method in which fragments comprising several amino acids are synthesized and then respective fragments are coupled. SY-001 may be synthesized by either one thereof.

A condensation method employed for the peptide synthesis can also be performed in accordance with the standard methods. Examples of the standard methods can include an azide method, a mixed acid anhydrate method, a DCC method, an active ester method, an oxidation and reduction method, a DPPA (diphenylphosphorylazide) method, a DDC additive (1-hydroxybenzotriazole, N-hydroxysuccinamide, N-hydroxy-5-norbornene-2,3-dicarboxyimide) method and Woodward method.

Upon the above peptide synthesis reaction, the amino acid not involved in the reaction or the carboxyl group in the peptide can be protected as lower alkyl ester such as methyl ester, ethyl ester and tert-butyl ester, and aralkyl ester such as benzyl ester, p-methoxybenzyl ester and p-nitrobenzyl ester generally by esterification.

The hydroxyl group in the amino acid such as tyrosine residue having a functional group in the side chain may be protected with acetyl group, benzyl group, benzyloxycarbonyl group or tert-butyl group, but is not always necessary to be protected. Furthermore, for example, guanidino group in arginine residue can be protected with an appropriate protecting group such as nitro, tosyl, p-methoxybenzenesulfonyl, methylene-2-surfonyl, benzyloxycarbonyl, isobornyloxycarbonyl or adamantyloxycarbonyl group.

A deprotection reaction of these protecting groups in the amino acid, the peptide and the polypeptide which is the active component of the eventually obtained pharmaceutical composition of the present invention, having the protecting group can be carried out in accordance with the methods commonly used such as contact reduction method and methods using liquid ammonia/sodium, hydrogen fluoride, hydrogen bromide, hydrogen chloride, trifluoroacetic acid, acetic acid, formic acid, methanesulfonic acid and the like.

SY-001 obtained in this way, which is the active component of the pharmaceutical composition of the present invention can be optionally purified in accordance with the various methods such as methods using an ion-exchange resin, partition chromatography and gel chromatography, and a countercurrent distribution method commonly used in the field of peptide chemistry.

(7) Pharmaceutical Composition of the Present Invention

It is important for the pharmaceutical composition of the present invention to contain SY-001 or the expressed product of the present invention as the active component. The pharmaceutical composition is useful as the pharmaceutical composition, particularly as a platelet aggregation inhibitor for inhibiting or blocking the condition in which the substance which induces the platelet aggregation increases in human blood vessel (particularly in coronary artery, aorta and cerebral artery) or an aggregation ability of platelets is facilitated in the blood vessel, or the condition in which the damage has occurred in the blood vessel and the platelets excessively aggregates at the damaged site.

The pharmaceutical composition is also useful, particularly as a platelet adhesion inhibitor for inhibiting or blocking the platelet adhesion to substance as an aggregating agent, such as collagen in which the substance which induces the adhesion with platelet in human blood vessel (particularly in coronary artery, aorta and cerebral artery) or an adhesive ability of platelets is facilitated in the blood vessel, or the condition in which the damage has occurred in the blood vessel and the platelets excessively aggregates at the damaged site.

The pharmaceutical composition of the present invention is useful as the therapeutic agent or the preventive agent for the pathological condition subsequent to the diseases and the complications thereof, e.g., acute coronary syndrome, myocardial infarction, cerebral embolism, chronic arterial obstruction, arterial sclerosis, ischemic cerebral infarction, angina, venous thrombosis, hypertension, pulmonary hypertension, cerebral infarction, pulmonary infarction, cardiac failure, nephritis, renal failure and subarachnoid hemorrhage caused by the formation of thrombus or embolus, by taking advantage of its inhibitory activity on the platelet aggregation and/or the platelet adhesion.

The pharmaceutical composition is useful for the prevention of the thrombus formation upon PTCA and stent placing, and the prevention of restenosis after placing the stent by enfolding this by, applying this on or embedding this in the stent itself, with expecting the inhibitory activity of SY-001 on the platelet aggregation and/or the platelet adhesion.

SY-001 or the expressed product of the present invention which is the active component in the pharmaceutical composition of the present invention has the inhibitory activity on the platelet aggregation and/or the platelet adhesion, and can be used for the procedure of the disease associated with the platelet aggregation and/or the platelet adhesion in the target cell or tissue by taking advantage of this action or activity. Examples of the target cell affected by such platelet aggregation and/or the platelet adhesion can include blood cells and platelets. Examples of the tissues comprising these cells can include coronary arterial vessel, cerebral arterial vessel, cervical arterial vessel, arterial vessel, venous vessel, peripheral arterial vessel, peripheral venous vessel, renal arterial vessel and hepatic arterial vessel.

According to the platelet aggregation inhibitory activity and/or the platelet adhesion inhibitory activity or the action to inhibit the platelet aggregation and/or the action to inhibit the platelet adhesion in the target cell, which the pharmaceutical composition of the present invention has, it is possible to treat or prevent the pathological conditions subsequent to the diseases and the complications thereof, e.g., myocardial infarction, cerebral embolism, chronic arterial obstruction, arterial sclerosis, ischemic cerebral infarction, angina, venous thrombosis, hypertension, pulmonary hypertension, cerebral infarction, pulmonary infarction, cardiac failure, nephritis, renal failure and subarachnoid hemorrhage caused by the formation of thrombus or embolus.

According to the platelet aggregation inhibitory activity and/or the platelet adhesion inhibitory activity of SY-001 on the platelet aggregation and/or the platelet adhesion, it is possible to prevent the thrombus formation upon PTCA and stent placing and prevent restenosis after placing the stent by enfolding the pharmaceutical composition of the present invention by, applying it on or embedding it in the stent itself.

The pharmaceutical composition of the present invention for the prevention of restenosis after placing the stent can be used as a cyclodextrin clathrate. The pharmaceutical composition of the present invention can also be used by applying (thickly applying or spraying) on a biodegradable resin which is a stent material or embedding in the stent itself.

SY-001 or the expressed product which is the active component in the pharmaceutical composition of the present invention also includes pharmaceutically acceptable salts thereof. Examples of such a salt include non-toxic alkali metal salts such as sodium, potassium, lithium, calcium, magnesium, barium and ammonium, alkali earth metal salts and ammonium salts. These salts can be produced in accordance with the standard methods. The above salts further include non-toxic acid addition salts obtained by the reaction of SY-001 or the expressed product of the present invention with an appropriate organic or inorganic acid. Examples of the representative non-toxic acid addition salts include hydrochloride, hydrobromide, sulfate, bisulfate, acetate, oxalate, valerate, oleate, laurate, borate, benzoate, lactate, malate, p-toluenesulfonate (tosylate), citrate, fumarate, succinate, tartrate, sulfonate, glycolate, ascorbate, benzenesulfonate and napsylate.

The pharmaceutical composition of the present invention is prepared into a pharmaceutical formulation form by making SY-001, the expressed product of the present invention or the salt thereof the active component, and containing a pharmaceutically effective amount thereof together with an appropriate pharmaceutical carrier or diluent.

As the pharmaceutical carrier used for preparing the pharmaceutical formulation, it is possible to exemplify excipients and diluents such as fillers, thickeners, binders, wetting agents, disintegrants, surface activators and lubricants. These are optionally selected and used depending on a dosage unit form of the resulting formulation. The particularly preferable pharmaceutical formulation is prepared by optionally using various ingredients, e.g., a stabilizer, a germicidal agent, a buffer, an isotonizing agent, a chelating agent, a pH adjuster, a surfactant and the like, used for usual protein formulations.

Examples of the stabilizer in the above include human serum albumin, common L-amino acids, saccharides and cellulose derivatives. These can be used alone or in combination with the surfactant. Particularly, by this combination, the stability of the active component is further enhanced in some cases.

The L-amino acid is not particularly limited, and any of glycine, cysteine, glutamic acid and the like may be used.

The saccharides are not particularly limited. For example, monosaccharides such as glucose, mannose, galactose and fructose, sugar alcohol such as mannitol, inositol and xylitol, disaccharides such as sucrose, maltose and lactose, polysaccharides such as dextran, hydroxypropyl starch, chondroitin sulfate and hyaluronic acid, and derivatives thereof can be used.

The surfactant is not particularly limited, and any of ionic surfactants and non-ionic surfactants can be used. Specific examples thereof include polyoxyethylene glycol sorbitan alkyl ester based, polyoxyethylene alkyl ether based, sorbitanmonoacyl ester based and fatty acid glyceride based surfactants.

The cellulose derivative is not particularly limited. Methylcellulose, ethylcellulose, hydroxyethylcellulose, hydroxypropylcellulose, hydroxypropylmethylcellulose and sodium carboxymethylcellulose and the like can be used.

An amount of the above saccharides to be added is about 0.0001 mg or more and preferably about 0.01 to 10 mg relative to 1 µg of the active component. The amount of the surfactant to be added is about 0.00001 mg or more and preferably about 0.0001 to 0.01 mg relative to 1 µg of the active component. The amount of human serum albumin to be added is about 0.0001 mg or more and preferably about 0.001 to 0.1 mg relative to 1 µg of the active component. The amount of the L-amino acid to be added is suitably about 0.001 to 10 mg relative to 1 µg of the active component. The amount of the cellulose derivative to be added is about 0.0001 mg or more and preferably about 0.001 to 0.1 mg relative to 1 µg of the active component.

The amount of the active component contained in the pharmaceutical formulation of the present invention is optionally selected from the broad range. It is suitable that the amount of the active component is typically about 0.00001 to 70% by weight and preferably about 0.0001 to 5% by weight in the formulation.

Various additives such as buffers, isotonizing agents and chelating agents can be added into the pharmaceutical formulation. Examples of the buffer include boric acid, phosphoric acid, acetic acid, citric acids-aminocaproic acid, glutamic acid and/or salts thereof (e.g., alkali metal salts such as sodium, potassium, calcium and magnesium salts and alkali earth metal salts). Examples of the isotonizing agent include sodium chloride, potassium chloride, saccharides and glycerine. Examples of the chelating agent include sodium edetate and citric acid.

The pharmaceutical formulation can be prepared as a solution formulation, and additionally can be made into a lyophilized dosage form obtained by lyophilizing the pharmaceutical formulation, which is prepared at an appropriate concentration in use by dissolving in the buffer containing saline.

The dosage unit form of the pharmaceutical formulation can be optionally selected depending on a therapeutic purpose. Representative examples thereof include solid dosage forms such as tablets, pills, powdered drugs, powders, granules and capsules, and liquid dosage forms such as solutions, suspensions, emulsions, syrups and elixirs. These are further categorized into oral agents, parenteral agents, nasal agents, vaginal agents, suppositories, sublingual agents and ointment agents depending on administration routes, and can be combined, molded and prepared in accordance with common methods. If necessary, coloring agents, preservatives, perfumes, flavoring agents and sweeteners and other pharmaceuticals can also be contained in the pharmaceutical formulation of the present invention.

An administration method of the pharmaceutical formulation is not particularly limited, and determined depending on various formulation forms, an age, a gender, other conditions and disease severity of a patient. For example, the tablet, the pill, the liquid, the suspension, the emulsion, the granule and the capsule are orally administered. An injectable agent is administered alone or in mixture with a common fluid replacement such as glucose and amino acid intravenously, if necessary intramuscularly, intracutaneously, subcutaneously or intraperitoneally alone. The suppository is administered intrarectally. The vaginal agent is administered in vagina, the nasal agent is administered in nose, the sublingual agent is administered in oral cavity, and the ointment agent is percutaneously administered topically.

A dose of the pharmaceutical formulation is not particularly limited and is optionally selected from the broad range depending on the desired therapeutic effect, the administration method, a treatment period, the age, the gender and the other conditions of the patient. Generally, it is preferable that the dose is determined so that the amount of the active component is typically about 0.01 µg to 10 mg, preferably about 0.1 µg to 1 mg per kg of body weight per day. The formulation can be administered by dividing into one to several times per day or intermittently.

(8) Screening of Substances (Agonist) to Facilitate Inhibitory Activity on the Platelet Aggregation and/or the Platelet Adhesion.

The present invention also provides the method for screening candidate compounds to facilitate the inhibitory activity on the platelet aggregation and/or the platelet adhesion.

The method is characterized by measuring the level of the platelet aggregation inhibitory activity and/or the platelet adhesion inhibitory activity of the polypeptide comprising the amino acid sequence of SEQ ID NO:1 or 3 or the polypeptide comprising the amino acid sequence having one or more amino acid deletions, insertions, substitutions or additions in the amino acid sequence of SEQ ID NO:1 or 3 and having the platelet aggregation inhibitory activity and/or the platelet adhesion inhibitory activity in the presence or absence of a subject substance, and selecting the subject substance which affect the platelet aggregation inhibitory activity and/or the platelet adhesion inhibitory activity as the agonist by comparing the measurement value in the presence of the subject substance with the measurement value in the absence of the subject substance.

The level of the platelet aggregation inhibitory action can be obtained by the platelet aggregation inhibition rate calculated from the measurement values obtained using the turbidimetric light-transmittance platelet aggregometer. More particularly, the human blood sample is collected using the syringe with the anticoagulant, and the human platelet-rich plasma (PRP) is prepared from the collected whole blood by centrifugation. A solution of purified SY-001 previously dissolved in PBS is added to PRP, which is then preincubated at 37° C. Subsequently, a collagen solution (supplied from NYCOMED) as the platelet aggregating agent is added thereto to aggregate the platelet, and the incubation is continued for a given time period. Then, a transmittancy of the solution is measured using the turbidimetric light-transmittance platelet aggregometer (MCM HEMA TRACER 313M: supplied from MC Medical) to make the platelet aggregation curve. The platelet aggregation inhibition rate can be calculated from this curve in each case of SY-001 or SY-001+ subject substance. As the above aggregating agent, it is possible to use ADP, CRP, convulxin, TRAP, epinephrine, arachidonic acid, U-46619, A23187 and the like in addition to collagen.

The level of the platelet adhesion inhibitory activity can be also obtained by the platelet adhesion inhibition rate calculated from the measurement values obtained using the Dc protein assay kit (Lowry's method [Lowry, O. et. al., *J. Biol. Chem.*, 193, 265 (1951)] BIO-RAD Laboratories). More particularly, the human blood sample is collected using the syringe with the anticoagulant, and the human platelet suspension is prepared from PRP obtained by the centrifugation of whole blood. A solution of purified SY-001 previously dissolved in PBS is added on 96 well plate coated with collagen and is incubated for 30 minutes at room temperature. After the incubation, the platelet suspension is added to well and is incubated for 45 minutes at room temperature. After the incubation, the incubation solution is removed with pipette from well and is washed it with PBS.

PBS solution containing 1% SDS is added to well, and the well is dried with air after the shaking and the stirring. Then, the distilled water is added to well, the protein amount of each well is measured using a Dc protein assay kit (BIO-RAD Laboratories), and a platelet adhesion inhibitory activity rate of SY-001 is calculated from an obtained measurement value based on the value in the control containing no SY-001 and calculating the platelet adhesion inhibitory activity of SY-001 from its platelet adhesion curve. The platelet adhesion inhibition rate can be calculated from this curve in each case of SY-001 or SY-001+subject substance. As the above platelet adhesion inducer, it is possible to use collagen.

The present invention also provides the method for screening the candidate substance which augment the platelet aggregation inhibitory activity of SY-001, comprising the following steps (1) to (4):
(1) a step of preparing the culture medium comprising the cell transformed with the expression vector of SY-001 and the platelet-rich plasma (PRP);
(2) a step of inducing the platelet aggregation by adding the platelet aggregating substance into the culture medium of the above (1) in the presence or absence of the subject substance;
(3) a step of measuring the levels of the platelet aggregation inhibition in the presence of the subject substance and in the absence of the subject substance in the above (2); and
(4) a step of selecting the subject substance as the candidate substance when the measurement value in the presence of the subject substance is larger than the measurement value in the absence of the subject substance.

The present invention also provides the method for screening the candidate substance which augments the platelet aggregation inhibitory action of the expressed product of the present invention, comprising the following steps (1) to (4):
(1) a step of preparing the culture medium comprising the cell containing the expressed product of the present invention and the platelet-rich plasma (PRP);
(2) a step of inducing the platelet aggregation by adding the platelet aggregating substance into the culture medium of the above (1) in the presence or absence of the subject substance;
(3) a step of measuring the levels of the platelet aggregation inhibition in the presence of the subject substance and in the absence of the subject substance in the above (2); and
(4) a step of selecting the subject substance as the candidate substance when the measurement value in the presence of the subject substance is larger than the measurement value in the absence of the subject substance.

The present invention also provides the method for screening the candidate substance which determines the platelet adhesion inhibitory activity of SY-001, comprising the following steps (1) to (4):
(1) a step of preparing the culture medium (on well) comprising the cell transformed with the expression vector of SY-001 and the well plate coating with platelet adhering substance (i.e. collagen);
(2) a step of inducing the platelet adhesion by adding the platelet suspension into the culture medium of the above (1) in the presence or absence of the subject substance;
(3) a step of measuring the levels of the platelet adhesion inhibition in the presence of the subject substance and in the absence of the subject substance in the above (2); and
(4) a step of selecting the subject substance as the candidate substance when the measurement value in the presence of the subject substance is larger than the measurement value in the absence of the subject substance.

The present invention further provides the method for screening the candidate substance which determines the platelet adhesion inhibitory action of the expressed product of the present invention, comprising the following steps (1) to (4):
(1) a step of preparing the culture medium (on well) comprising the cell containing the expressed product of the present invention and the well plate coating with platelet adhering substance (i.e. collagen);
(2) a step of inducing the platelet adhesion by adding the platelet suspension into the culture medium of the above (1) in the presence or absence of the subject substance;
(3) a step of measuring the levels of the platelet adhesion inhibition in the presence of the subject substance and in the absence of the subject substance in the above (2); and
(4) a step of selecting the subject substance as the candidate substance when the measurement value in the presence of the subject substance is larger than the measurement value in the absence of the subject substance.

The screening method of the present invention can be carried out by practically applying high throughput screening technology. According to the practical application of this technology, for example, in the screening for an accelerator of the platelet aggregation inhibitory activity and/or the platelet adhesion inhibitory activity, a preparation (including SY-001 and labeled ligand of the polypeptide) with any of a synthetic reaction mixture, a cell fraction, a blood fraction, e.g., platelet-rich plasma or platelet suspension is incubated in the presence or absence of the subject substance to be screened. Whether the subject substance agonizes the action of SY-001 or antagonizes the action of SY-001 is detected by the decrease of the bound labeled ligand. The activity level of SY-001 can be detected by a reporter system of colorimetric label (is not limited to this), the incorporation of a reporter gene responsible to the activity change of the polynucleotide or the polypeptide, or a binding assay publicly known in the art.

A competitive assay in which SY-001 or the other mutant [e.g., SY-001 (151-269), SY-001 (21-269)] and the other platelet aggregation inhibitor (e.g., acetylsalicylic acid, cilostazol) are combined with the compound which is bound thereto can be used for screening the candidate compound as the accelerator of the platelet aggregation inhibitory activity.

A competitive assay in which SY-001 or the other mutant [e.g., SY-001 (151-269), SY-001 (21-269)] and the other platelet adhesion inhibitor (e.g., Ticlopidine) are also combined with the compound which is bound thereto can be used for screening the candidate compound as the accelerator of the platelet adhesion inhibitory activity.

The subject substance (candidate compound) screened by the screening method of the present invention is highly likely the agonist of SY-001 as the accelerator of the platelet aggregation inhibitory activity and/or the platelet adhesion inhibitory activity.

The agonist can be the substance to increase the platelet aggregation inhibitory activity and/or the platelet adhesion inhibitory activity measured by the presence thereof in the screening system of the present invention.

Specific examples of these subject substances include oligopeptides, proteins, antibodies, RNA molecules, siRNA, non-peptide compounds (synthetic compounds), fermented products, cell extracts (plant extracts, animal extracts) and plasma. These substances may be those newly developed or known substances.

Examples of the platelet aggregation inhibitory substance and/or the platelet adhesion inhibitory substance include inorganic or organic low molecular compounds, naturally occurring or synthetic peptides and polypeptides, or peptides and polypeptides prepared by the gene recombination technology, which augment the activity of SY-001 by binding thereto. The sense DNA molecule for the DNA molecule encoding SY-001, administered directly in vivo or administered in the form inserted in the recombinant vector is also included in the above platelet aggregation inhibitory substance and/or the platelet adhesion inhibitory substance.

The candidate substance having the activity to augment the platelet aggregation inhibitory activity, and/or the platelet adhesion inhibitory activity screed in accordance with the screening method of the present invention is evaluated as follows. That is, the candidate substance which increases or facilitates the platelet aggregation inhibitory activity and/or the platelet adhesion inhibitory activity by about 20% or more, preferably about 30% or more and more preferably about 50% or more compared with the control (absence of the subject substance) can be evaluated as the compound to facilitate the platelet aggregation inhibitory activity and/or the platelet adhesion inhibitory activity.

The compound to facilitate the platelet aggregation inhibitory activity and/or the platelet adhesion inhibitory activity is thought to be useful as the therapeutic agent or the preventive agent for the pathological condition subsequent to the diseases and the complications thereof, e.g., myocardial infarction, cerebral embolism, chronic arterial obstruction, arterial sclerosis, ischemic cerebral infarction, angina, venous thrombosis, hypertension, pulmonary hypertension, cerebral infarction, pulmonary infarction, cardiac failure, nephritis, renal failure and subarachnoid hemorrhage caused by the formation of thrombus or embolus.

Among the substances to facilitate the platelet aggregation inhibitory activity and/or the platelet adhesion inhibitory activity, obtained by the screening method of the present invention, it is thought that there also is the substance itself having the activity to inhibit the platelet aggregation induced by the platelet aggregating substance in vivo, and/or to inhibit the platelet adhesion induced by the platelet adhering substance in vivo and such a substance is thought to be useful as the platelet aggregation inhibitor and/or the platelet adhesion inhibitor in various field including the pharmaceutical field.

(9) Kit for Screening

The present invention can provide a kit for screening the agonist for SY-001, characterized by comprising the platelet-rich plasma, SY-001 (including the expressed product of the present invention) and the platelet aggregating agent as the constituents.

The kit for screening of the present invention comprises (1) SY-001 (e.g., the polypeptide having the amino acid sequence of SEQ ID NO:1 or 3) or the expressed product of the present invention (e.g., the expressed product of the DNA molecule encoding SY-001, of the DNA sequence of SEQ ID NO:2 or 4), (2) the cell culture medium comprising the platelet-rich plasma and (3) the platelet aggregating agent as the essential ingredients. Similarly to the kits for screening of this type, the kit can comprise various reagents such as cell culture media, reaction diluents, staining agents, buffers, fixing solutions and washing solutions as other optional ingredients.

Specific examples of the kit of the present invention include those comprising the following constituents 1 to 3:

Constituent 1: cells (SY-001 expressing cells, cultured cells comprising *Escherichia coli* cells or insect cells transformed with the polynucleotide (DNA molecule) encoding SY-001) cultured in a 60 mm dish at 0.5 to $1 \times 10^5$ cells/well at 37° C. under 5% $CO_2$ using MOPS buffer containing EGTA-Na;

Constituent 2: the substance (e.g., collagen, ADP) to induce the platelet aggregation; and Constituent 3: platelet-rich plasma.

In the screening method using the kit for screening of the present invention, the platelet aggregation inhibition rate is detected in the platelet-rich plasma per well unit visual field of the well in which the test substance (subject substance, medicament candidate substance) has been added. Then, the platelet aggregation inhibition rate is detected in the well in which the test substance has not been added. Subsequently, the significant difference is tested between the former rate and the latter rate. These measurement and evaluation can be carried out in accordance with the standard methods.

The present invention can also provide a kit for screening the agonist for SY-001, characterized by containing the platelet adhering agent (i.e. collagen), SY-001 (including the expressed product of the present invention) and the platelet suspension as the constituents.

The kit for screening of the present invention comprises (1) SY-001 (e.g., the polypeptide having the amino acid sequence of SEQ ID NO:1 or 3) or the expressed product of the present invention (e.g., the expressed product of the DNA molecule encoding SY-001, of the DNA sequence of SEQ ID NO:2 or 4), (2) the platelet adhering substance (i.e. collagen) and (3) the platelet suspension as the essential ingredients. Similarly to the kits for screening of this type, the kit can comprise various reagents such as cell culture media, reaction diluents, staining agents, buffers, fixing solutions and washing solutions as other optional ingredients.

Specific examples of the kit of the present invention include those comprising the following constituents 1 to 3:

Constituent 1: cells (SY-001 expressing cells, cultured cells comprising *Escherichia coli* cells or insect cells transformed with the polynucleotide (DNA molecule) encoding SY-001) cultured in a 60 mm dish at 0.5 to $1 \times 10^5$ cells/well at 37° C. under 5% $CO_2$ using PBS buffer;

Constituent 2: the platelet adhering substance (e.g., collagen, ADP) to induce the platelet adhesion; and Constituent 3: platelet suspension.

In the screening method using the kit for screening of the present invention, the platelet adhesion inhibition rate is detected as the level of the platelet adhesion to collagen per well unit visual field of the well in which the test substance (subject substance, medicament candidate substance) has been added. Then, the platelet adhesion inhibition rate is detected in the well in which the test substance has not been added. Subsequently, the significant difference is tested between the former rate and the latter rate. These measurement and evaluation can be carried out in accordance with the standard methods.

EXAMPLES

The present invention will be described in more detail with reference to the following Examples. These Examples are only for exemplification and do not limit the present invention.

Example 1

1. Preparation of cDNA Library from Salivary Gland in *Anopheles stephensi*

Female *Anopheles stephensi* (SDA500 strain) 3 to 7 days after eclosion was made suck blood in a mouse (BALB/c strain purchased from CLEA Japan Inc.). Wings, feet, a head portion and an abdominal portion were removed from the mosquito 6 hours after sucking the blood, and only a breast portion including the salivary gland was stored in liquid nitrogen. At the time when the breast portions of 300 mosquitoes were collected, RNA was extracted using RNeasy Midi Kit (QIAGEN). A library was made by collecting poly A-added RNA, making cDNA using reverse transcriptase, adding restriction enzyme sites (EcoRI and HindIII sites) at both ends and incorporating into λ SCREEN-1 Cloning Kits (Novagen).

2. Imunoscreening of Salivary Gland cDNA Library

*Escherichia coli* (ER-1647, Takara) was infected with each phage of the above library, and screened using an anti-*Anopheles stephensi* salivary gland antibody as a probe. The anti-*Anopheles stephensi* salivary gland antibody was made by immunizing a rabbit with a homogenate of the *Anopheles stephensi* salivary gland together with Freund's adjuvant.

A positive clone obtained by the screening was infected to *Escherichia coli* ER-1647 and amplified Then the phage was removed and an inserted portion was cloned into a plasmid pSCREEN-1b(+) (Novagen) using CreMediated Plasmid Excision (Novagen). A base sequence of the inserted portion was sequenced utilizing DNA portions (SP6 promoter primer: SEQ ID NO:10, product code No. TKR3867, Takara Bio, and T7 terminator primer: SEQ ID NO:11, product code No. NV432, Novagen) added at both ends of pSCREEN using 310 Genetic Analyzer supplied from ABI.

As a result of analyzing the base sequence, it was found that a cloned gene fragment contained a stop codon but deleted an initiation codon. In order to obtain the deleted 5' region of SY-001 cDNA, 5'-RACE method [Frohman, M. A., et al., PNASC, 8, 8998-9002(1988)] was performed using X screen phage DNA extracted from the salivary gland cDNA library as a template and using primers, SP6 promoter primer (SEQ ID NO: 10) and pAnS-1 primer of SEQ ID NO12 to clone a DNA fragment of about 470 bp. This DNA fragment was overlapped with the DNA fragment obtained in the above screening, and further contained the initiation codon. The two DNA fragments were ligated to determine the entire base sequence of the DNA molecule encoding SY-001.

An ORF found in the cDNA encoded 269 amino acid residues of a putative protein of 28.5 kDa and contained 807 bp. This protein was predicted to be the protein secreted to the saliva because it was predicted from the deduced amino acid sequence that this protein was an acidic protein with pI=3.8, 21 amino acid residues at the N terminus were hydrophobic and exhibited a signal peptide-like sequence and the C terminus had no membrane anchor region.

This deduced amino acid sequence is shown in SEQ ID NO:5. The base sequence of the DNA molecule encoding the amino acid sequence is shown in SEQ ID NO:6.

3. Expression of SY-001 by Recombinant DNA and Purification Thereof (1) Production of SY-001 (22-269)

A DNA fragment encoding the amino acid residues at positions 22 to 269 of SY-001 (SEQ ID NO:5) was amplified by PCR. The salivary gland cDNA shown in the above 1 was used as the template. The primer pAnSG-F7 (SEQ ID NO13) used had NcoI site (CCATGG) at 3rd to 8th sites from the 5' end, and the primer pAnSG-R1 (SEQ ID NO14) used had NotI site (GCGGCCGC) at 2nd to 9th sites from the 5' end. Then, the DNA fragment was cloned into pENTR/D-TOPO (Invitrogen) to construct the plasmid pENTR-SY-001-Exon 1-4.

Subsequently, an SY-001 DNA fragment (about 760 bp) obtained by cleaving pENTR-SY-001-Exon 1-4 with NcoI and NotI was inserted into NcoI/NotI site of pET32-b(+) (Novagen) to construct the plasmid pET32-SY-001-Exon 1-4.

*Escherichia coli* BL21 (DE3) (Novagen) was transformed with this pET32-SY-001-Exon 1-4, and the resulting transformant was cultured with shaking in 6 mL of LB medium (LBA) containing 50 µg/mL of ampicillin for 15 hours at 37° C. Then, the cultured medium was added into 600 mL of LBA, which was then cultured with shaking 4 hours at 37° C. for. Subsequently 6 mL of 100 mM IPTG was added into the culture medium, which was further cultured with shaking for 4 hours at 37° C. The resulting culture medium was centrifuged at 6,000×g for 15 minutes, and a supernatant was removed. A resulting pellet was lysed by adding 40 mL of 6 M guanidine hydrochloride thereto. A resulting bacterial solution was centrifuged at 30,000×g for 25 minutes, and the supernatant was collected. To this, 1.8 mL of Ni-NTA (QIAGEN) was added, which was then stirred for 15 hours at 4° C. The mixture was centrifuged at 3,000×g for 3 minutes, the supernatant was removed and Ni-NTA was collected. A 6M urea-TBS solution (6 M urea, 150 mM NaCl, 50 mM Tris-HCl [pH7.5]) containing 10 mM imidazole was added to collected Ni-NTA. The resulting mixture was centrifuged at 3,000×g for 3 minutes, and the supernatant was removed. The resulting Ni-NTA was packed into a column.

The SY-001 Exon 1-4 protein was eluted from the column as follows. That is, 2 mL of 6M urea-TBS solutions containing 20 mM, 50 mM, 100 mM and 200 mM imidazole, respectively were sequentially run through the column, and respective fractions were collected. A portion of each fraction was electrophoresed on 12% SDS-PAGE, and then stained with Coomassie staining to determine the fraction which contained the SY-001 Exon 1-4 protein. This fraction was dialyzed against PBS for 48 hours. The amount of the protein was quantified using BCA Protein Assay Kit (PIERCE), and a yield was 5.0 mg.

The amino acid sequence of the recombinant protein obtained in this way was as shown in SEQ ID NO:7. The amino acid sequence at positions 1 to 162 and the amino acid sequence at positions 410 to 420 are the amino acid sequences derived from a thioredoxin protein and pET32-b(+) containing a His tag sequence, respectively. The amino acid sequence of SY-001 (22 to 269) of the present invention is located at positions 162 to 409.

(2) Production of SY-001 (148-269)

PCR with pET32-SY-001 Exon1-4 prepared in the above (1) as the template was performed using the primers pAnSG-F8 (SEQ ID NO:15) and pAnSG-R1 (SEQ ID NO14). The resulting DNA fragment (382 bp) was cloned into pENTR/D-TOPO (Invitrogen) to construct the plasmid pENTR-SY-001 Exon 3-4. The plasmid pENTR-SY-001 Exon 3-4 was cleaved with NcoI/NotI to obtain the DNA fragment of 372 bp. This was inserted into the NcoI/NotI sites of pET32 (b)+ (Novagen) to construct the plasmid pET32-SY-001 Exon 3-4.

*Escherichia coli* BL21 (DE3) (Novagen) was transformed with pET32-SY-001-Exon 3-4 obtained above, and the resulting transformant was cultured with shaking in 6 mL of LB medium (LBA) containing 50 μg/mL of ampicillin for 15 hours at 37° C. Then, the cultured medium was added into 600 mL of LBA, which was then cultured with shaking for 4 hours at 37° C. Subsequently 6 mL of 100 mM IPTG was added into the culture medium, which was further cultured with shaking for 4 hours at 37° C. The resulting culture medium was centrifuged at 6,000×g for 15 minutes, and the supernatant was removed. The resulting pellet was lysed by adding 40 mL of 6 M guanidine hydrochloride thereto. The resulting bacterial solution was centrifuged at 30,000×g for 25 minutes, and the supernatant was collected. To this, 1.8 mL of Ni-NTA (QIAGEN) was added, which was then stirred for 15 hours at 4° C. The mixture was centrifuged at 3,000×g for 3 minutes, the supernatant was removed and Ni-NTA was collected. The 6M urea-TBS solution (6 M urea, 150 mM NaCl, 50 mM Tris-HCl [pH7.5]) containing 10 mM imidazole was added to collected Ni-NTA. The resulting mixture was centrifuged at 3,000×g for 3 minutes, and the supernatant was removed. The resulting Ni-NTA was packed into the column.

The SY-001 Exon 3-4 protein was eluted from the column as follows. That is, 2 mL of the 6M urea-TBS solutions containing 20 mM, 50 mM, 100 mM and 200 mM imidazole, respectively were sequentially run through the column, and respective fractions were collected. A portion of each fraction was electrophoresed on 12% SDS-PAGE, and then stained with Coomassie staining to determine the fraction which contained the SY-001 Exon 3-4 protein. This fraction was dialyzed against PBS for 48 hours. The amount of the protein was quantified using BCA Protein Assay Kit (PIERCE), and the yield was 1.8 mg.

The amino acid sequence of the recombinant protein obtained in this way was as shown in SEQ ID NO:8, and had the amino acid sequence contained 293 amino acid residues. In this amino acid sequence, the amino acid sequence at positions 1 to 160 and the amino acid sequence at positions 283 to 293 are the amino acid sequences derived from a thioredoxin protein and pET32-b(+) containing a His tag sequence, respectively. The amino acid sequence of SY-001 (148 to 269) is located at positions 161 to 282.

Example 2

Production of Recombinant SY-001 (21-269) Using Baculovirus Expression System (1) Production of Baculovirus SY-001 (21-269)

A DNA fragment encoding the polypeptide at positions 21 to 269 of SY-001 (SEQ ID NO:1) was amplified by PCR using the salivary gland cDNA shown in Example 1, 1 as the template. The primer pAnSG-F10 (SEQ ID NO:16) used had BamHI site (GGATCC) at 5th to 10th sites from the 5' end and a FLAG sequence at 12th G to 41st A. The primer pAnSG-R1 (SEQ ID NO:14) used had NotI site (GCGGCCGC) at 2nd to 9th sites from the 5' end. The DNA fragment was cloned into pENTR/D-TOPO (Invitrogen) to construct the plasmid pENTR-SY-001-Exon 1-4.

Subsequently, an SY-001 fragment (780 bp) obtained by cleaving pENTR-SY-001-Exon 1-4 with BamHI/NotI was inserted into BamHI/NotI sites of pBACgus-1 (Novagen) to construct a baculovirus transfer vector plasmid pBACgus-SY-001-Exon 1-4.

Recombinant baculovirus was made using a recombinant baculovirus making kit (BacVector-2000 Transfection Kit, Novagen) by co-transfecting Sf9 cells with the above baculovirus transfer vector plasmid pBACgus-SY-001-Exon 1-4 and BacVector-2000 DNA. The prepared recombinant baculovirus was designated as AcNPV-SY-001-Exon 1-4.

That is, the Sf9 cells were cultured at $1 \times 10^7$ cells per 150 mm petri dish, and infected with AcNPV-SY-001-Exon 1-4 at an infection multiplicity of about 5. After 3 to 4 days, about 250 mL of the culture supernatant was collected from 10 of 150 mm petri dishes, and 1.5 mL of Ni-NTA (QIAGEN) was added thereto, which was then stirred for 15 hours at 4° C. The mixture was centrifuged at 3,000×g for 3 minutes and the supernatant was discarded. Ni-NTA was collected, and 50 mL of a TBS solution (150 mM NaCl, 50 mM Tris-HCl [pH7.5]) containing 10 mM imidazole was added thereto. The resulting mixture was further centrifuged at 3,000×g for 3 minutes and the supernatant was discarded. The obtained Ni-NTA was packed in the column.

The SY-001 Exon 1-4 protein was eluted from the column as follows. That is, 2 mL of the TBS solutions containing 20 mM, 50 mM, 100 mM and 200 mM imidazole, respectively were sequentially run through the column, and respective fractions were collected. A portion of each fraction was electrophoresed on 12% SDS-PAGE, and then stained with Coomassie staining to determine the fraction which contained the SY-001 Exon 1-4 protein. This fraction was dialyzed against PBS for 48 hours. The amount of the protein was quantified using BCA Protein Assay Kit (PIERCE), and the yield was 0.8 mg.

The amino acid sequence of the recombinant protein SY-001 (21-269) obtained in this way is shown in SEQ ID NO:9. In the sequence, the sequence at positions 1 to 10 is the FLAG sequence, the amino acid sequence at positions 11 to 259 is the sequence of SY-001 (21-269), and the sequence at positions 260 to 270 is the sequence derived from pBACgus-1 containing the His tag sequence.

Example 3

The inhibitory action of SY-001 on the platelet aggregation was evaluated by measuring the platelet aggregation in platelet-rich plasma (PRP) using a turbidimetric light-transmittance platelet aggregometer.

An outline of the method is as follows. That is, first, a blood sample was collected from a healthy donor using a syringe with anticoagulant, and the platelet-rich plasma (PRP) was prepared by centrifuging the collected whole blood. The prepared PRP was mixed and pre-incubated with an SY-001 solution [PBS solution in which SY-001 having the amino acid sequence of SEQ ID NO:7 prepared in Example 1, 3-(1) had been dissolved] or PBS as the control, and subsequently the platelets were aggregated by adding a platelet aggregating agent. As the platelet aggregating agent, ADP (supplied from Sigma), collagen (supplied from NYCOMED), CRP (supplied from Peptide Institute Inc.), convulxin (supplied from Alexis), TRAP (supplied from Sawaday Technology Co.), epinephrine (supplied from Daiichi Pharmaceutical Co., Ltd.), arachidonic acid (supplied from Sigma), U-46619 (supplied from Cayman) or A23187 (supplied from Sigma) was used, respectively.

Then, the platelet aggregation rate was measured over 5 minutes using the turbidimetric light-transmittance platelet aggregometer (MCM HEMA TRACER 313M: supplied from MC Medical), and the maximum aggregation rate was obtained in the measurement for 5 minutes. The platelet aggregation inhibition rate (%) of SY-001 was calculated in accordance with the following formula.

Platelet aggregation inhibition rate $(\%) = (1 - As/Ac) \times 100$

As: Maximum platelet aggregation rate in PRP with SY-001
Ac: Maximum platelet aggregation rate in PRP alone as control Details of the above manipulation are as shown in the following (a) to (c).

(a) First, 60 mL of blood was collected from the healthy donor using the syringe with 6 mL of 3.8% sodium citrate as the coagulant. Subsequently, the blood was centrifuged at 1,100 rpm for 10 minutes, and a human platelet-rich plasma (PRP) layer as an upper layer was transferred into another test tube. A remaining lower layer portion was centrifuged at 3,000 rpm for 10 minutes, and a resulting upper clear yellow layer (platelet-poor plasma, PPP) was transferred into another test tube. The mixture in which the number of platelets had been adjusted at $3 \times 10^8$/mL was made by mixing PRP and PPP obtained above, and used in the subsequent measurement. This mixture is referred to as a "PRP measurement sample" in the following measurement.

The platelet aggregation rate of the platelet aggregometer was set so that the light transmittance in PPP was 100% of the platelet aggregation rate and the light transmittance in PRP was 0% of the platelet aggregation rate.

(b) Determination of Collagen Concentration and Measurement of Platelet Aggregation Inhibitory Activity First, an aggregation cuvette in which 200 μL of the PRP measurement sample containing no SY-001 had been added was set in the platelet aggregometer, and incubated for 2 minutes at 37° C. Subsequently, 22.2 μL of a collagen solution (supplied from NYCOMED GmBH, Moriya Sangyo) was added thereto, and the platelet aggregation rate was continuously measured over 5 minutes at 37° C. The highest platelet aggregation rate in 5 minutes was made the maximum platelet aggregation rate. In the collagen solution, the concentrations at 5 to 20 μg/mL (final concentrations in the PRP measurement sample were 0.5 to 2 μg/mL) were employed as submaximum concentrations at which 70% of the maximum platelet aggregation rate was induced.

c) Then, (i) SY-001 (22-269) [having the amino acid sequence of SEQ ID NO:7 prepared in Example 1,3-(1)] prepared at 30 nM, 100 nM and 300 nM, respectively, (ii) SY-001 (148-269) [having the amino acid sequence of SEQ ID NO:8 prepared in Example 1, 3-(2)] prepared at 100 nM, 300 nM and 1000 nM, respectively or (iii) PBS (137 mM NaCl, 2.7 mM KCl, 8.1 mM $Na_2HPO_4$, 1.5 mM $KH_2PO_4$) as the control was added into each cuvette in which 200 μL of the PRP measurement sample had been added. Each mixture was set in the platelet aggregometer, and incubated for 2 minutes at 37° C. Subsequently, 22.2 μL of the collagen solution at a given concentration determined above was added thereto, and the platelet aggregation rate was measured over 5 minutes from the addition thereof.

The result of the platelet aggregation inhibitory activity of SY-001 (22-269) induced by the stimulation with collagen is shown in FIG. 1. The result of the platelet aggregation inhibitory activity of SY-001 (148-269) induced by the stimulation with collagen is also shown in FIG. 2.

In each figure, a horizontal axis represents a time course (−0.5 to 5 minutes) from 30 seconds before the addition of collagen, and a vertical axis represents the platelet aggregation rate (%).

In FIG. 1, the curve 1 shows the result in the case of adding SY-001 (22-269) at a concentration of 300 nM, the curve (2) shows the result of SY-001 (22-269) at 100 nM, the curve (3) shows the result of SY-001 (22-269) at 30 nM, and the curve (4) shows the result of the control.

Figure 2:
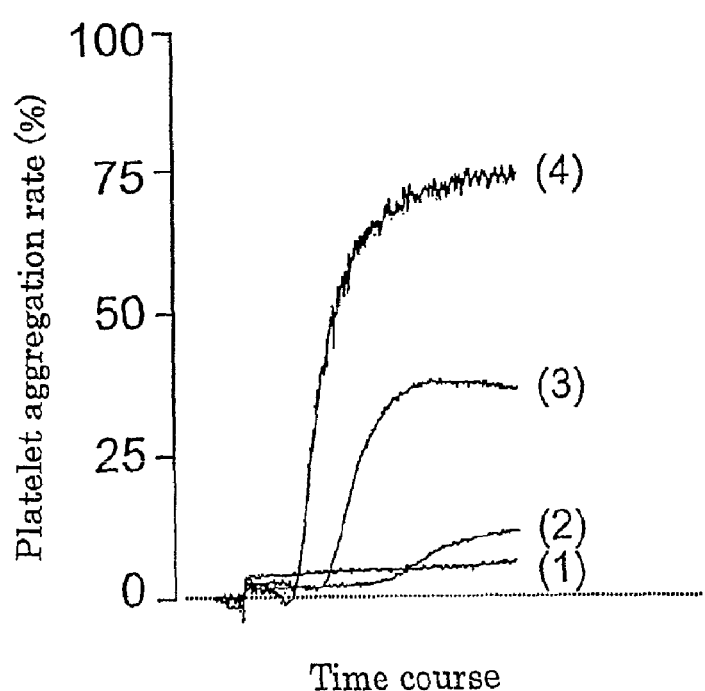
FIG. 2 shows the platelet aggregation inhibitory activity of SY-001 produced in Example 1, 3(2) induced by stimulation with collagen.

In FIG. 2, the curve 1 shows the result in the case of adding SY-001 (148-269) at a concentration of 1000 nM, the curve (2) shows the result of SY-001 (148-269) at 300 nM, the curve (3) shows the result of SY-001 (148-269) at 100 nM, and the curve (4) shows the result of the control.

As is evident from the results shown in these figures, it has been shown that SY-001 of the present invention reduces the platelet aggregation induced by the stimulation with collagen as its addition amount is increased, i.e., SY-001 has the platelet aggregation inhibitory activity.

The same experiments as the above were performed using the recombinant protein SY-001 (21-269) produced in the baculovirus expression system in Example 2. As a result, substantially the same results as those shown in FIG. 1 were obtained. Consequently, it is obvious that the SY-001 of the present invention has the platelet aggregation inhibitory activity.

In the experiments using the above SY-001 (21-269), the platelet aggregation rates were obtained by changing the concentrations of SY-001 (21-269) from 3 nM to 1000 nM. Then, log-logit analysis for the platelet aggregation inhibitory activity ($IC_{50}$) of SY-001 (21-269) was performed using SAS software (SAS Institute, Japan, Release 8.1). As a result, $IC_{50}$ of SY-001 (21-269) was calculated to be 25 nM.

From the above results, it has been speculated that an epitope portion present in the C terminal side between positions 148 and 269 in the amino acid sequence of SY-001 of SEQ ID NO:5 might contribute to the platelet aggregation inhibitory activity of SY-001 of the present invention.

Example 4

Synthesis of SY-001 Mutant

SY-001 is synthesized below by solid phase synthesis method using Fmoc (9-fluorenylmethyloxycarbonyl) method.

A synthetic polypeptide having the desired number of amino acid residues from the N terminus to C terminus of the amino acid sequence of SEQ ID NO:5 can be obtained by reacting in a continuous flow mode using TBTU [2-(1H-Benzotriazole-1-yl)-1,1,3,3-tetramethyluronium tetrafluoroborate] and HOBt [1-Hydroxybenzotriazole hydrate] as active reagents.

If necessary, the resulting synthetic polypeptide can be dissolved in dimethylsulfoxide and further diluted with acetonitrile.

Formulation Example 1

(1) The pharmaceutical composition of the present invention in the injectable formulation was prepared by adding and mixing 100 μg/mL of SY-001 (having the amino acid sequence of SEQ ID NO:8), 0.01 mg/mL of Tween 80 (Polyoxyethylene(20)Sorbitan Monooleate; Polysorbate 80), 15 mg/mL of dextran 40, 0.1 mg/mL of cysteine and 1.0 mg/mL of HSA (human serum albumin) in 0.01 M citric acid-sodium citrate buffer (pH 6.0), filtrating the mixture (using a membrane filter of 0.22 μm), then sterilely dispensing the filtrate by 1 mL in a vial and lyophilizing it. The formulation can be used by dissolving in 1 mL of saline in use.

(2) The pharmaceutical composition of the present invention in the injectable formulation was prepared by adding 10 μg/0.1 mL of SY-001 (having the amino acid sequence of SEQ ID NO:8), 5 mg of cysteic acid and 1 mg of human serum albumin (HSA) per vial in distilled water for the injection, filling the resulting solution in one vial by 1 mL and lyophilizing it.

Action of SY-001 on Platelet Adhesion to Collagen

An SY-001 solution (50 LL) at 3, 10, 30, 100, 300, 1000 or 3000 nM was added into a 96-well plate coated with 40 μg/mL of collagen (NYCOMED GmBH), and incubated for 30 minutes at room temperature. After the incubation, 50 μL of a platelet suspension ($6 \times 10^8$/mL cells) was added to each well, and incubated for 45 minutes at room temperature. After the incubation, the solution in each well was removed using a pipette, and the wells were washed with 200 μL of PBS. Subsequently, 20 μL of PBS containing 1% SDS was added to each well, which was then stirred with shaking and dried in air at 45° C. Then, 5 μL of distilled water was added to each well, and a protein concentration in the well was measured using Dc protein assay kit (BIO-RAD).

Figure 3:
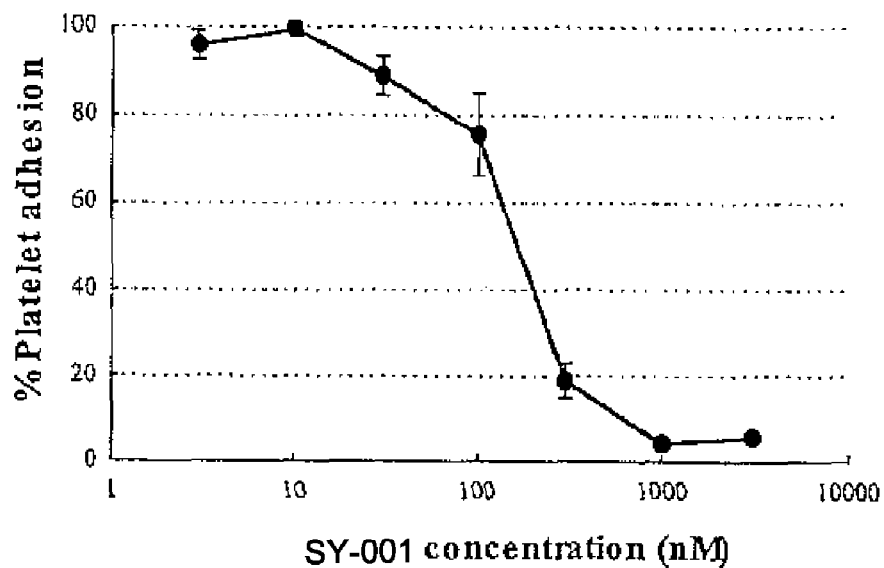
FIG. 3 shows the platelet adhesion inhibitory activity of SY-001 produced in Examples 1 and 3, which inhibits the platelet adhesion to collagen in Example 5.

The results are shown in FIG. 3.

As is shown in FIG. 3, it was identified that SY-001 of the present invention inhibited the platelet adhesion to collagen in a dose dependent manner, and that SY-001 exhibited the potent inhibitory action on the platelet adhesion particularly at doses of 300 μg/mL or more.

Binding Capacity of SY-001 to Collagen

A blocking solution (300 μL) was added to each well of a 96-well plate (NUNC, 152038) coated with collagen or a 96-well plate (NUNC, 260895) not coated, and incubated for one hour at room temperature. The solution in each well was removed, and 100 μL of an SY-001 protein solution at 3, 10, 30, 100 or 300 nM was added to each well, and incubated for one hour at room temperature. The solution in each well was removed, 200 μL of 2% sucrose was added to the well, and incubated for 5 minutes at room temperature. The solution in each well was removed, and the well was dried. Subsequently, 100 μL of a reconstituted Ni-HRP solution (ExpressDetector Nickel-HRP supplied from KPL) was added to each well, and incubated for 30 minutes at room temperature. After washing with a wash buffer, 100 μL of ABTS Peroxidase Substrate was added to each well, and gently mixed with shaking. After the termination of the reaction, 100 μL of 1% SDS was added, and an absorbance at a wavelength of 405 to 410 nm was measured using a microplate reader.

Figure 4:
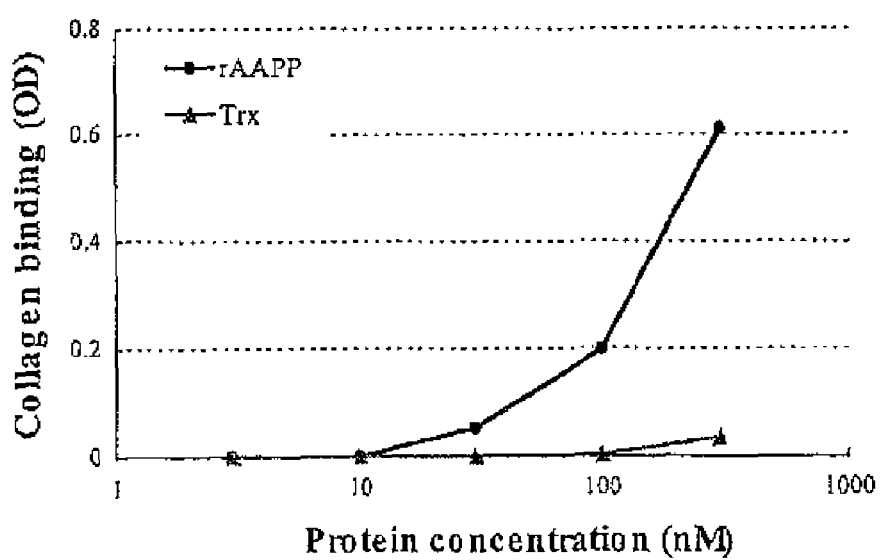
FIG. 4 shows that SY-001 produced in Examples 1 and 3 has the binding ability to collagen in Example 6.

The results are shown in FIG. 4. Triangles represent a reaction curve of the empty vector as the control. As is shown in FIG. 4, it was identified that SY-001 had the binding capacity to collagen.

As in the above, it could be identified that SY-001 of the present invention had not only the inhibitory action on the platelet aggregation but also the inhibitory action on the platelet adhesion to collagen. It could also be identified that SY-001 of the present invention had the binding capacity to collagen.

From these results, the pharmaceutical composition comprising SY-001 of the present invention as the active component can be the useful pharmaceutical composition as the therapeutic agent and the preventive agents for myocardial infarction, pulmonary embolism, cerebral infarction and the like.

Platelet adhesion inhibitory action and collagen binding capacity of recombinant SY-001

FIG. 3: SY-001 inhibits the platelet adhesion to collagen.
FIG. 4: SY-001 has the binding capacity to collagen.

Sequencing List Free Text

SEQ ID NO: 10 represents the SP6 promoter primer sequence, SEQ ID NO: 11 represents the T7 terminator primer sequence, SEQ ID NO: 12 represents the pAnS-1 primer sequence, SEQ ID NO: 13 represents the pAnSG-F7 primer sequence, SEQ ID NO: 14 represents the pAnSG-R1 primer sequence, SEQ ID NO: 15 represents the pAnSG-F8 primer sequence and SEQ ID NO: 16 represents the pAnSG-F10 primer sequence.

INDUSTRIAL APPLICABILITY

According to the present invention, it is possible to provide the pharmaceutical composition containing SY-001 or the expressed product of the present invention as the active component. The composition of the present invention is thought to be useful as a therapeutic agent or a preventive agent for pathological conditions subsequent to various diseases, e.g., the diseases and complications caused by thrombus or embolus, e.g., acute coronary syndrome, myocardial infarction, cerebral embolism, chronic arterial obstruction, arterial sclerosis, ischemic cerebral infarction, angina, venous thrombosis, hypertension, pulmonary hypertension, cerebral infarction, pulmonary infarction, cardiac failure, nephritis, renal failure and subarachnoid hemorrhage, in which SY-001 and the polynucleotide (DNA molecule) encoding SY-001 polypeptide are involved.

Furthermore, the composition of the present invention is thought to be useful for the prevention of the thrombus formation upon PTCA and stent placing, and for the prevention of restenosis after placing the stent by enfolding SY-001 by, applying SY-001 on or embedding SY-001 in the stent itself.

By utilizing SY-001 and the DNA molecule encoding SY-001 provided by the present invention, it is possible to screen the agonist for the polypeptide or the expressed product by the DNA molecule (expressed product of the present invention), i.e., screen the substance having the activity to facilitate the inhibitory activity inherent for these proteins on the platelet aggregation and/or the platelet adhesion as the candidate compound.

The invention claimed is:

1. An isolated polypeptide consisting of the amino acid sequence of SEQ ID NO:3.

2. An expressed product, wherein said product is expressed by a polynucleotide consisting of the DNA sequence of SEQ ID NO:4.

3. A composition comprising the polypeptide of claim 1 as an active component, and at least one carrier.

4. A kit comprising components (1)-(3):
(1) the polypeptide of claim 1;
(2) a cell culture medium comprising platelet-rich plasma; and
(3) a platelet aggregating agent.

5. A kit comprising components (1)-(3):
(1) the polypeptide of claim 1;
(2) a platelet adhering substance; and
(3) a platelet suspension.

6. A composition comprising the expressed product of claim 2 as an active component, and at least one carrier.

7. A kit comprising components (1)-(3):
(1) the expressed product of claim 2;
(2) a cell culture medium comprising platelet-rich plasma; and
(3) a platelet aggregating agent.

8. A kit comprising components (1)-(3):
(1) the expressed product of claim 2;
(2) a platelet adhering substance; and
(3) a platelet suspension.

* * * * *

UNITED STATES PATENT AND TRADEMARK OFFICE
CERTIFICATE OF CORRECTION

PATENT NO. : 8,309,512 B2  
APPLICATION NO. : 13/215004  
DATED : November 13, 2012  
INVENTOR(S) : Shigeto Yoshida and Toshiki Sudo Page 1 of 1

It is certified that error appears in the above-identified patent and that said Letters Patent is hereby corrected as shown below:

Title page, item [75]

The second Inventor's address is currently listed as

Toshiki Sudo, Sokushima(JP)

To be deleted: "Sokushima"

To be replaced by: Tokushima

Signed and Sealed this  
Eleventh Day of March, 2014

Michelle K. Lee  
*Deputy Director of the United States Patent and Trademark Office*